(12) United States Patent
Helf et al.

(10) Patent No.: US 8,469,244 B2
(45) Date of Patent: Jun. 25, 2013

(54) OVERCAP AND SYSTEM FOR SPRAYING A FLUID

(75) Inventors: Thomas A. Helf, New Berlin, WI (US); Edward L. Paas, Los Altos, CA (US); Brent D. Madsen, Providence, UT (US); Paul E. Furner, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 502 days.

(21) Appl. No.: 11/893,476

(22) Filed: Aug. 16, 2007

(65) Prior Publication Data

US 2009/0045219 A1 Feb. 19, 2009

(51) Int. Cl.
*G04C 23/00* (2006.01)

(52) U.S. Cl.
USPC ........... 222/645; 222/646; 222/648; 222/649; 222/482; 222/402.21; 222/504

(58) Field of Classification Search
USPC ............. 222/52, 61, 645, 646, 647, 648, 649, 222/402.21, 182, 504
See application file for complete search history.

(56) References Cited

U.S. PATENT DOCUMENTS

| | | |
|---|---|---|
| 2,608,319 A | 8/1952 | Petry |
| 2,613,108 A | 10/1952 | Kraus |
| 2,928,573 A | 3/1960 | Edelstein |
| 3,018,056 A | 1/1962 | Montgomery |
| 3,115,277 A | 12/1963 | Montague, Jr. |
| 3,127,060 A | 3/1964 | Vosbikian et al. |
| 3,139,218 A * | 6/1964 | Cairelli .................... 222/647 |
| 3,165,238 A | 1/1965 | Wiley |
| 3,180,532 A | 4/1965 | Michel |
| 3,185,356 A | 5/1965 | Venus, Jr. |
| 3,199,732 A | 8/1965 | Strachan |
| 3,228,609 A | 1/1966 | Edelstein et al. |
| 3,240,389 A | 3/1966 | Genua |
| 3,269,602 A | 8/1966 | Weber, III |
| 3,273,610 A | 9/1966 | Frost |
| 3,289,886 A | 12/1966 | Goldsholl et al. |
| 3,305,134 A | 2/1967 | Carmichael et al. |
| 3,326,418 A | 6/1967 | Kropp |
| 3,329,314 A | 7/1967 | Kolodziej |
| 3,368,717 A | 2/1968 | Weber, III |
| 3,398,864 A | 8/1968 | Kolodziej |
| 3,411,670 A | 11/1968 | Mangel |
| 3,419,189 A | 12/1968 | Iketani |

(Continued)

FOREIGN PATENT DOCUMENTS

| | | |
|---|---|---|
| EP | 656230 | 6/1995 |
| EP | 0676133 | 10/1995 |

(Continued)

OTHER PUBLICATIONS

International Search Report and Written Opinion PCT/US2008/009663 dated Dec. 23, 2008.

*Primary Examiner* — Kevin P Shaver
*Assistant Examiner* — Daniel R Shearer

(57) ABSTRACT

A volatile material dispenser includes a housing adapted to be releasably mounted on a container having a tilt-activated valve stem. The housing includes a discharge orifice. A drive unit is disposed within the housing, wherein the drive unit is activated in response to a signal from at least a sensor, and wherein the drive unit is adapted to radially displace the tilt-activated valve stem in response to the signal.

5 Claims, 20 Drawing Sheets

U.S. PATENT DOCUMENTS

| | | | |
|---|---|---|---|
| 3,455,485 A | 7/1969 | Crownover | |
| 3,477,613 A | 11/1969 | Mangel | |
| 3,497,108 A | 2/1970 | Mason | |
| 3,497,110 A | 2/1970 | Bombero et al. | |
| 3,542,248 A | 11/1970 | Mangel | |
| 3,543,122 A | 11/1970 | Klebanoff et al. | |
| 3,584,766 A | 6/1971 | Hart et al. | |
| 3,589,562 A | 6/1971 | Buck | |
| 3,589,563 A | 6/1971 | Carragan et al. | |
| 3,591,058 A | 7/1971 | Johnston | |
| 3,617,214 A | 11/1971 | Dolac | |
| 3,620,023 A | 11/1971 | Schmid | |
| 3,627,176 A | 12/1971 | Sailors | |
| 3,632,020 A | 1/1972 | Nixon, Jr. et al. | |
| 3,643,836 A | 2/1972 | Hunt | |
| 3,658,209 A | 4/1972 | Freeman et al. | |
| 3,664,548 A | 5/1972 | Broderick | |
| 3,666,144 A | 5/1972 | Winder | |
| 3,677,441 A | 7/1972 | Nixon, Jr. et al. | |
| 3,690,519 A | 9/1972 | Wassilieff | |
| 3,722,749 A | 3/1973 | Ishida | |
| 3,726,437 A | 4/1973 | Siegel | |
| 3,732,509 A | 5/1973 | Florant et al. | |
| 3,739,944 A | 6/1973 | Rogerson | |
| 3,756,465 A | 9/1973 | Meshberg | |
| 3,794,216 A | 2/1974 | Buck | |
| 3,817,429 A | 6/1974 | Smrt | |
| 3,841,525 A * | 10/1974 | Siegel | 222/649 |
| 3,870,274 A | 3/1975 | Broe | |
| 3,871,557 A | 3/1975 | Smrt | |
| 3,885,712 A | 5/1975 | Libit | |
| 3,929,259 A | 12/1975 | Fegley et al. | |
| 3,952,916 A | 4/1976 | Phillips | |
| 3,968,905 A | 7/1976 | Pelton | |
| 3,974,941 A | 8/1976 | Mettler | |
| 3,980,205 A | 9/1976 | Smart | |
| 4,004,550 A | 1/1977 | White et al. | |
| 4,006,844 A | 2/1977 | Corris | |
| 4,063,664 A | 12/1977 | Meetze, Jr. | |
| 4,064,573 A | 12/1977 | Calderone | |
| 4,068,575 A | 1/1978 | Difley et al. | |
| 4,068,780 A | 1/1978 | Fegley | |
| 4,077,542 A | 3/1978 | Petterson | |
| 4,096,974 A | 6/1978 | Haber et al. | |
| 4,184,612 A | 1/1980 | Freyre | |
| 4,235,373 A | 11/1980 | Clark | |
| 4,238,055 A | 12/1980 | Staar | |
| 4,275,821 A | 6/1981 | Lanno et al. | |
| 4,396,152 A | 8/1983 | Abplanalp | |
| 4,415,797 A | 11/1983 | Choustoulakis | |
| 4,483,466 A | 11/1984 | Gutierrez | |
| 4,544,086 A | 10/1985 | Hill et al. | |
| 4,658,985 A | 4/1987 | Madsen et al. | |
| 4,702,418 A * | 10/1987 | Carter et al. | 239/101 |
| 4,877,989 A | 10/1989 | Drews et al. | |
| 4,967,935 A | 11/1990 | Celest | |
| 4,989,755 A | 2/1991 | Shiau | |
| 4,993,570 A | 2/1991 | Julian et al. | |
| 5,012,961 A | 5/1991 | Madsen et al. | |
| 5,014,881 A | 5/1991 | Andris | |
| 5,018,963 A | 5/1991 | Diederich | |
| 5,025,962 A | 6/1991 | Renfro | |
| 5,029,729 A | 7/1991 | Madsen et al. | |
| 5,038,972 A | 8/1991 | Muderlak et al. | |
| 5,055,822 A | 10/1991 | Campbell et al. | |
| 5,098,291 A | 3/1992 | Curtis et al. | |
| 5,134,961 A | 8/1992 | Giles et al. | |
| 5,154,323 A | 10/1992 | Query et al. | |
| 5,198,157 A | 3/1993 | Bechet | |
| 5,221,025 A | 6/1993 | Privas | |
| 5,249,718 A | 10/1993 | Muderlak | |
| 5,297,988 A | 3/1994 | Nishino et al. | |
| 5,337,926 A | 8/1994 | Drobish et al. | |
| 5,337,929 A | 8/1994 | van der Heijden | |
| 5,342,584 A | 8/1994 | Fritz et al. | |
| 5,353,744 A | 10/1994 | Custer | |
| 5,364,028 A | 11/1994 | Wozniak | |
| 5,383,580 A | 1/1995 | Winder | |
| RE34,847 E | 2/1995 | Muderlak et al. | |
| 5,392,768 A | 2/1995 | Johansson et al. | |
| 5,397,028 A | 3/1995 | Jesadanont | |
| 5,445,324 A | 8/1995 | Berry et al. | |
| 5,447,273 A | 9/1995 | Wozniak | |
| 5,447,277 A | 9/1995 | Schlüter et al. | |
| 5,449,117 A | 9/1995 | Muderlak et al. | |
| 5,489,047 A | 2/1996 | Winder | |
| 5,503,303 A | 4/1996 | LaWare et al. | |
| 5,522,722 A | 6/1996 | Diederich | |
| 5,531,344 A | 7/1996 | Winner | |
| 5,540,359 A | 7/1996 | Gobbel | |
| 5,542,605 A | 8/1996 | Campau | |
| 5,549,228 A | 8/1996 | Brown | |
| 5,588,565 A | 12/1996 | Miller | |
| 5,601,235 A | 2/1997 | Booker et al. | |
| 5,622,162 A | 4/1997 | Johansson et al. | |
| 5,673,825 A | 10/1997 | Chen | |
| 5,676,283 A | 10/1997 | Wang | |
| 5,685,456 A | 11/1997 | Goldstein | |
| 5,695,091 A | 12/1997 | Winings et al. | |
| 5,702,036 A | 12/1997 | Ferrara, Jr. | |
| 5,743,251 A | 4/1998 | Howell et al. | |
| 5,772,074 A | 6/1998 | Dial et al. | |
| 5,787,947 A | 8/1998 | Hertsgaard | |
| 5,791,524 A | 8/1998 | Demarest | |
| 5,810,265 A | 9/1998 | Cornelius et al. | |
| 5,823,390 A | 10/1998 | Muderlak et al. | |
| 5,842,602 A | 12/1998 | Pierpoint | |
| 5,853,129 A | 12/1998 | Spitz | |
| 5,884,808 A | 3/1999 | Muderlak et al. | |
| 5,908,140 A | 6/1999 | Muderlak et al. | |
| 5,922,247 A | 7/1999 | Shoham et al. | |
| 5,924,597 A | 7/1999 | Lynn | |
| 5,938,076 A | 8/1999 | Ganzeboom | |
| 5,964,403 A | 10/1999 | Miller et al. | |
| 6,000,658 A | 12/1999 | McCall, Jr. | |
| 6,006,957 A | 12/1999 | Kunesh | |
| 6,036,108 A | 3/2000 | Chen | |
| 6,039,212 A | 3/2000 | Singh | |
| 6,089,410 A | 7/2000 | Ponton | |
| 6,145,712 A | 11/2000 | Benoist | |
| 6,182,904 B1 | 2/2001 | Ulczynski et al. | |
| 6,216,925 B1 | 4/2001 | Garon | |
| 6,220,293 B1 | 4/2001 | Rashidi | |
| 6,237,812 B1 | 5/2001 | Fukada | |
| 6,249,717 B1 | 6/2001 | Nicholson et al. | |
| 6,254,065 B1 | 7/2001 | Ehrensperger et al. | |
| 6,260,739 B1 | 7/2001 | Hsiao | |
| 6,267,297 B1 | 7/2001 | Contadini et al. | |
| 6,276,574 B1 | 8/2001 | Smrt | |
| 6,293,442 B1 | 9/2001 | Mollayan | |
| 6,293,474 B1 | 9/2001 | Helf et al. | |
| 6,321,742 B1 | 11/2001 | Schmidt et al. | |
| 6,338,424 B2 | 1/2002 | Nakamura et al. | |
| 6,343,714 B1 | 2/2002 | Tichenor | |
| 6,394,310 B1 | 5/2002 | Muderlak et al. | |
| 6,409,093 B2 | 6/2002 | Ulczynski et al. | |
| 6,419,122 B1 | 7/2002 | Chown | |
| 6,454,185 B2 | 9/2002 | Fuchs | |
| 6,478,199 B1 | 11/2002 | Shanklin et al. | |
| 6,510,561 B1 | 1/2003 | Hammond et al. | |
| 6,517,009 B2 | 2/2003 | Yahav | |
| 6,533,141 B1 | 3/2003 | Petterson et al. | |
| 6,540,155 B1 | 4/2003 | Yahav | |
| 6,554,203 B2 | 4/2003 | Hess et al. | |
| 6,567,613 B2 | 5/2003 | Rymer | |
| 6,588,627 B2 | 7/2003 | Petterson et al. | |
| 6,612,464 B2 | 9/2003 | Petterson et al. | |
| 6,616,363 B1 | 9/2003 | Guillaume et al. | |
| 6,619,562 B2 | 9/2003 | Hamaguchi et al. | |
| 6,644,507 B2 | 11/2003 | Borut et al. | |
| 6,645,307 B2 | 11/2003 | Fox et al. | |
| 6,669,105 B2 | 12/2003 | Bryan et al. | |
| 6,688,492 B2 | 2/2004 | Jaworski et al. | |
| 6,694,536 B1 | 2/2004 | Haygreen | |
| 6,701,663 B1 | 3/2004 | Hughes et al. | |
| 6,708,849 B1 | 3/2004 | Carter et al. | |
| D488,548 S | 4/2004 | Lablaine | |

| | | |
|---|---|---|
| 6,722,529 B2 | 4/2004 | Ceppaluni et al. |
| 6,739,479 B2 | 5/2004 | Contadini et al. |
| 6,769,580 B2 | 8/2004 | Muderlak et al. |
| 6,776,968 B2 | 8/2004 | Edwards et al. |
| 6,785,911 B1 | 9/2004 | Percher |
| 6,790,408 B2 | 9/2004 | Whitby et al. |
| 6,832,701 B2 | 12/2004 | Schiller |
| 6,837,396 B2 | 1/2005 | Jaworski et al. |
| 6,843,465 B1 | 1/2005 | Scott |
| 6,877,636 B2 | 4/2005 | Speckhart et al. |
| 6,918,512 B2 | 7/2005 | Kondoh |
| 6,926,002 B2 | 8/2005 | Scarrott et al. |
| 6,926,172 B2 | 8/2005 | Jaworski et al. |
| 6,926,211 B2 | 8/2005 | Bryan et al. |
| 6,938,796 B2 | 9/2005 | Blacker et al. |
| 6,971,560 B1 | 12/2005 | Healy et al. |
| 6,974,091 B2 | 12/2005 | McLisky |
| 6,978,947 B2 | 12/2005 | Jin |
| D513,433 S | 1/2006 | Lemaire |
| 6,997,349 B2 | 2/2006 | Blacker et al. |
| 7,000,853 B2 | 2/2006 | Fugere |
| 7,028,917 B2 | 4/2006 | Buthier |
| 7,032,782 B1 | 4/2006 | Ciavarella et al. |
| D520,623 S | 5/2006 | Lablaine |
| 7,044,337 B1 | 5/2006 | Kou |
| 7,051,455 B2 | 5/2006 | Bedford |
| D525,693 S | 7/2006 | Butler et al. |
| D527,472 S | 8/2006 | Barraclough et al. |
| D532,891 S | 11/2006 | Buthier et al. |
| 7,141,125 B2 | 11/2006 | McKechnie et al. |
| D536,059 S | 1/2007 | King et al. |
| D536,082 S | 1/2007 | Pugh |
| 7,168,631 B2 | 1/2007 | Jones |
| 7,182,227 B2 | 2/2007 | Poile et al. |
| D537,914 S | 3/2007 | King et al. |
| D538,915 S | 3/2007 | Anderson et al. |
| 7,192,610 B2 | 3/2007 | Hughes et al. |
| 7,195,139 B2 | 3/2007 | Jaworski et al. |
| D540,931 S | 4/2007 | Luo |
| 7,223,361 B2 | 5/2007 | Kvietok et al. |
| 7,249,720 B2 | 7/2007 | Mathiez |
| 2002/0020756 A1 | 2/2002 | Yahav |
| 2002/0130146 A1 | 9/2002 | Borut et al. |
| 2003/0089734 A1 | 5/2003 | Eberhardt et al. |
| 2003/0132254 A1 | 7/2003 | Giangreco |
| 2004/0011885 A1 | 1/2004 | McLisky |
| 2004/0028551 A1 | 2/2004 | Kvietok et al. |
| 2004/0033171 A1 | 2/2004 | Kvietok et al. |
| 2004/0035949 A1 | 2/2004 | Elkins et al. |
| 2004/0074935 A1 | 4/2004 | Chon |
| 2004/0155056 A1 | 8/2004 | Yahav |
| 2004/0219863 A1 | 11/2004 | Willacy |
| 2005/0004714 A1 | 1/2005 | Chen |
| 2005/0023287 A1 | 2/2005 | Speckhart et al. |
| 2005/0139624 A1 | 6/2005 | Hooks et al. |
| 2005/0155985 A1 | 7/2005 | Meyer |
| 2005/0201944 A1 | 9/2005 | Kvietok et al. |
| 2005/0224596 A1 | 10/2005 | Panopoulos |
| 2005/0247735 A1* | 11/2005 | Muderlak et al. ............ 222/190 |
| 2005/0252930 A1 | 11/2005 | Contadini et al. |
| 2005/0279853 A1 | 12/2005 | McLeisch et al. |
| 2006/0011737 A1 | 1/2006 | Amenos et al. |
| 2006/0037532 A1 | 2/2006 | Eidson |
| 2006/0060615 A1 | 3/2006 | McLisky |
| 2006/0076366 A1 | 4/2006 | Furner et al. |
| 2006/0081661 A1 | 4/2006 | Lasserre et al. |
| 2006/0083632 A1 | 4/2006 | Hammond et al. |
| 2006/0118658 A1 | 6/2006 | Corkhill et al. |
| 2006/0124477 A1 | 6/2006 | Cornelius et al. |
| 2006/0140901 A1 | 6/2006 | McKechnie |
| 2006/0151546 A1 | 7/2006 | McLisky |
| 2006/0153733 A1 | 7/2006 | Sassoon |
| 2006/0175341 A1 | 8/2006 | Rodrian |
| 2006/0175357 A1 | 8/2006 | Hammond |
| 2006/0175426 A1 | 8/2006 | Schramm et al. |
| 2006/0191955 A1 | 8/2006 | McLisky |
| 2006/0196576 A1 | 9/2006 | Fleming et al. |
| 2006/0210421 A1 | 9/2006 | Hammond et al. |
| 2006/0219740 A1 | 10/2006 | Bayer |
| 2006/0229232 A1 | 10/2006 | Contadini et al. |
| 2006/0243762 A1 | 11/2006 | Sassoon |
| 2007/0012718 A1 | 1/2007 | Schramm et al. |
| 2007/0062980 A1 | 3/2007 | Bates et al. |
| 2007/0071933 A1 | 3/2007 | Gavelli et al. |
| 2007/0087953 A1 | 4/2007 | McKechnie et al. |
| 2007/0093558 A1 | 4/2007 | Harper et al. |
| 2007/0138326 A1 | 6/2007 | Hu |
| 2007/0158359 A1 | 7/2007 | Rodrian |

FOREIGN PATENT DOCUMENTS

| | | |
|---|---|---|
| EP | 0826607 | 3/1998 |
| EP | 0826608 | 3/1998 |
| EP | 1184083 | 3/2002 |
| EP | 1214949 | 6/2002 |
| EP | 1316514 | 6/2003 |
| EP | 1382399 | 1/2004 |
| EP | 1430958 | 6/2004 |
| EP | 1522506 | 4/2005 |
| EP | 1328757 | 5/2006 |
| EP | 1695720 | 8/2006 |
| EP | 1702512 | 9/2006 |
| EP | 1702513 | 9/2006 |
| EP | 1709980 | 10/2006 |
| EP | 1726315 | 11/2006 |
| FR | 1497250 | 10/1967 |
| FR | 2216810 | 8/1974 |
| GB | 1033025 | 6/1966 |
| GB | 1531308 | 11/1978 |
| JP | 56037070 | 4/1981 |
| JP | 56044060 | 4/1981 |
| JP | 56044061 | 4/1981 |
| JP | 56044062 | 4/1981 |
| JP | 56070865 | 6/1981 |
| JP | 57174173 | 10/1982 |
| JP | 62109760 | 7/1987 |
| JP | 01-223904 | 9/1989 |
| JP | 03-085169 | 4/1991 |
| JP | 03-085170 | 4/1991 |
| JP | 10216577 | 8/1998 |
| JP | 2001048254 | 2/2001 |
| JP | 2002068344 | 3/2002 |
| JP | 2002113398 | 4/2002 |
| JP | 2003246380 | 9/2003 |
| JP | 2003311191 | 11/2003 |
| JP | 2004298782 | 10/2004 |
| JP | 2005081223 | 3/2005 |
| WO | WO 91/15409 | 10/1991 |
| WO | WO 95/19304 | 7/1995 |
| WO | WO95/29106 | 11/1995 |
| WO | WO 99/34266 | 7/1999 |
| WO | WO 00/47335 | 8/2000 |
| WO | WO 00/64802 | 11/2000 |
| WO | WO 00/75046 | 12/2000 |
| WO | WO00/75046 | 12/2000 |
| WO | WO 00/78467 | 12/2000 |
| WO | WO 01/26448 | 4/2001 |
| WO | WO 02/40177 | 5/2002 |
| WO | WO 02/40376 | 5/2002 |
| WO | WO 02/072161 | 9/2002 |
| WO | WO 02/079679 | 10/2002 |
| WO | WO 02/087976 | 11/2002 |
| WO | WO 02/094014 | 11/2002 |
| WO | WO 03/037748 | 5/2003 |
| WO | WO03/037748 | 5/2003 |
| WO | WO03/037750 | 5/2003 |
| WO | WO 03/037750 | 5/2003 |
| WO | WO03/042068 | 5/2003 |
| WO | WO 03/042068 | 5/2003 |
| WO | WO 03/062094 | 7/2003 |
| WO | WO03/062094 | 7/2003 |
| WO | WO03/062095 | 7/2003 |
| WO | WO 03/062095 | 7/2003 |
| WO | WO 03/068412 | 8/2003 |
| WO | WO 03/068413 | 8/2003 |
| WO | WO03/082709 | 10/2003 |
| WO | WO 03/086902 | 10/2003 |
| WO | WO 03/086947 | 10/2003 |
| WO | WO 03/099682 | 12/2003 |

| | | | | | | |
|---|---|---|---|---|---|---|
| WO | WO 03/104109 | 12/2003 | | WO | WO2006074454 A2 | 7/2006 |
| WO | WO 2004/043502 | 5/2004 | | WO | WO2006/087514 | 8/2006 |
| WO | WO 2004/067963 | 8/2004 | | WO | WO2006/087515 | 8/2006 |
| WO | WO 2004/073875 | 9/2004 | | WO | WO2006/095131 | 9/2006 |
| WO | WO 2004/093927 | 11/2004 | | WO | WO 2006/104993 | 10/2006 |
| WO | WO 2004/093928 | 11/2004 | | WO | WO 2006/105652 | 10/2006 |
| WO | WO2005/011560 | 2/2005 | | WO | WO 2006/108043 | 10/2006 |
| WO | WO2005/014060 | 2/2005 | | WO | WO2006/134353 | 12/2006 |
| WO | WO 2005/018691 | 3/2005 | | WO | WO2007/028954 | 3/2007 |
| WO | WO 2005/023679 | 3/2005 | | WO | WO 2007/029044 | 3/2007 |
| WO | WO2005/027630 | 3/2005 | | WO | WO2007/036724 | 4/2007 |
| WO | WO2005/048718 | 6/2005 | | WO | WO2007/045826 | 4/2007 |
| WO | WO2005/070474 | 8/2005 | | WO | WO2007/045827 | 4/2007 |
| WO | WO 2005/072059 | 8/2005 | | WO | WO2007/045828 | 4/2007 |
| WO | WO 2005/072522 | 8/2005 | | WO | WO2007/045831 | 4/2007 |
| WO | WO2005/079583 | 9/2005 | | WO | WO2007/045832 | 4/2007 |
| WO | WO2005/084721 | 9/2005 | | WO | WO2007/045834 | 4/2007 |
| WO | WO2006/005962 | 1/2006 | | WO | WO2007/045835 | 4/2007 |
| WO | WO 2006/012248 | 2/2006 | | WO | WO2007/045859 | 4/2007 |
| WO | WO2006/013321 | 2/2006 | | WO | WO 2007/052016 | 5/2007 |
| WO | WO2006/013322 | 2/2006 | | WO | WO 2007/064188 | 6/2007 |
| WO | WO 2006/044416 | 4/2006 | | WO | WO 2007/064189 | 6/2007 |
| WO | WO2006/051267 | 5/2006 | | WO | WO 2007/064197 | 6/2007 |
| WO | WO2006/054103 | 5/2006 | | WO | WO 2007/064199 | 6/2007 |
| WO | WO2006/056762 | 6/2006 | | | | |
| WO | WO2006/058433 | 6/2006 | | | | |
| WO | WO2006/064187 | 6/2006 | | | | |

\* cited by examiner

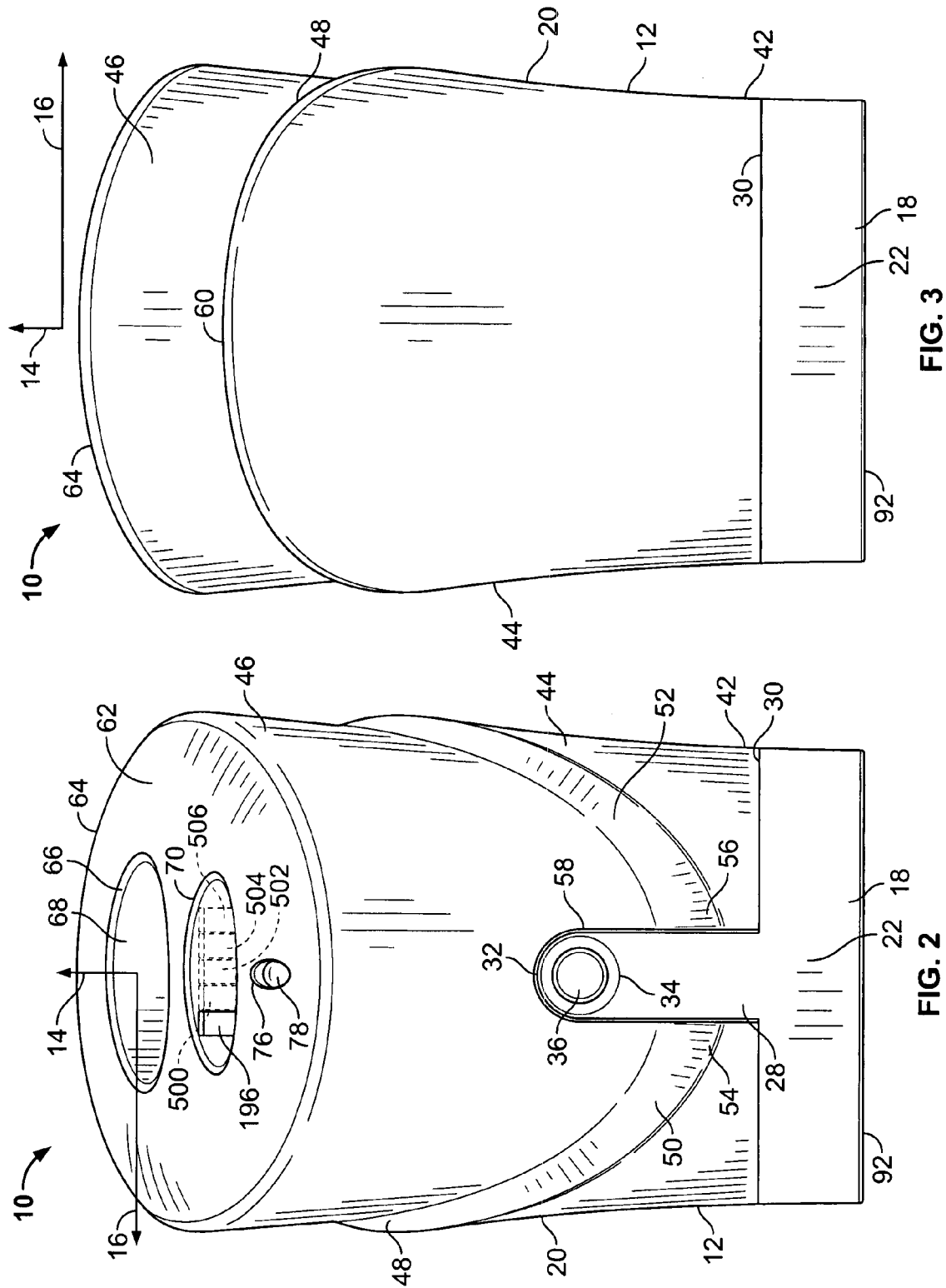

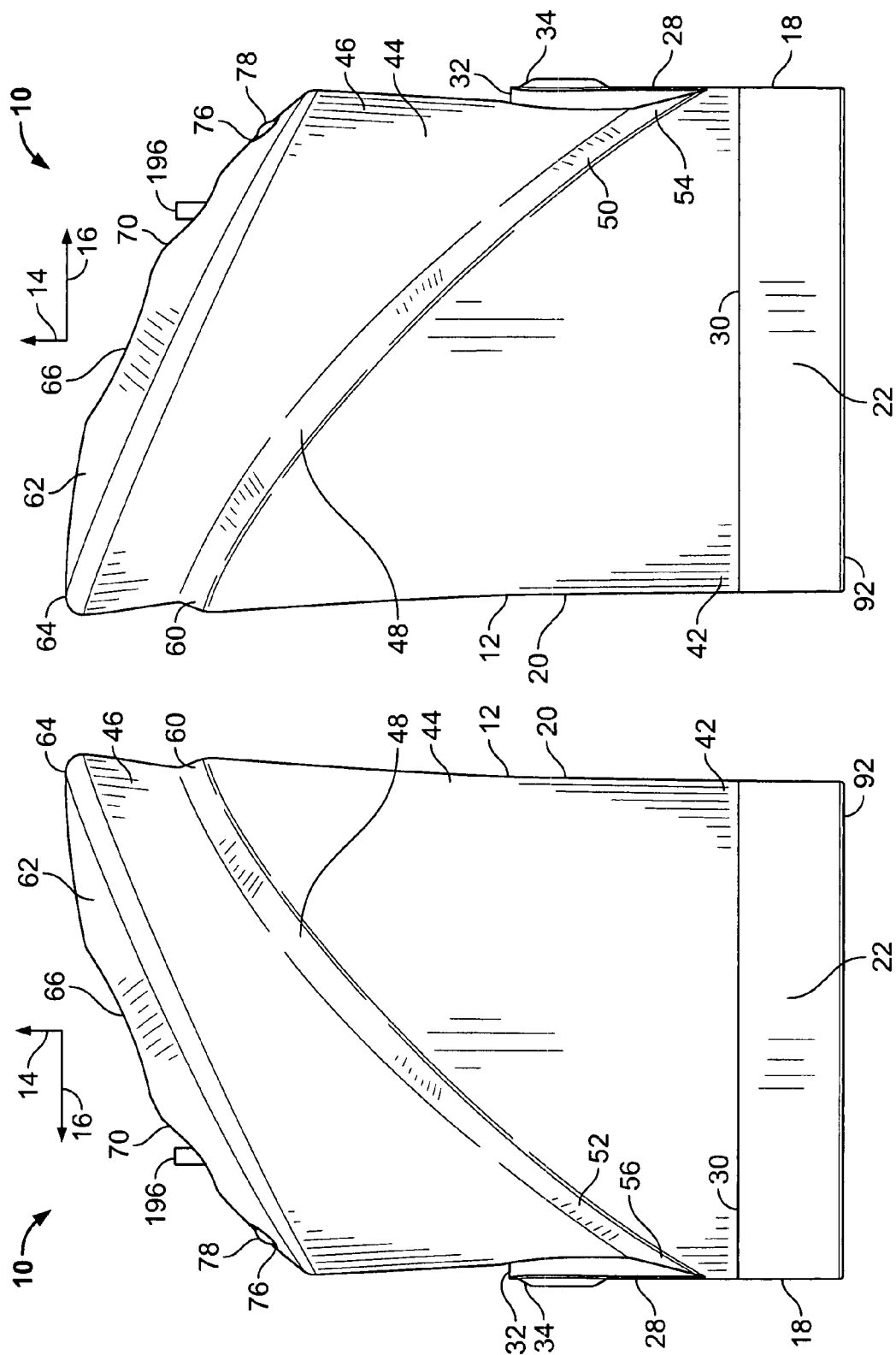

OVERCAP AND SYSTEM FOR SPRAYING A FLUID

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates generally to an overcap for a container, and more particularly to an overcap adapted to be placed on an aerosol container having a tilt-activated valve stem.

2. Description of the Background of the Invention

Aerosol containers are commonly used to store and dispense volatile materials such as air fresheners, deodorants, insecticides, germicides, decongestants, perfumes, and the like. The volatile material is stored under compression and typically in a liquid state within a container. A release valve on the container controls release of the volatile material contained under compression therein. The release valve typically has a valve stem that outwardly extends from the valve, wherein the valve is activated by the valve stem and the volatile material flows out of the container through the valve stem. In such a release valve, the valve is activated by a displacement of the valve stem with respect to a valve body. The valve stem may be displaced along a longitudinal axis of the valve stem, i.e., axially, or the valve stem may be tilted or displaced in a direction transverse to the longitudinal axis of the valve stem, i.e., radially.

Activation of a release valve may be accomplished by an automated system or manually. In manual activation, a user may adjust an activation force applied to the valve as required to achieve a desired release. Therefore, consideration of applied force requirements is generally less important to design of manually activated release valves. Conventional actuator mechanisms may include motor driven linkages that apply downward pressure to depress the nozzle and open the valve within the container. Typically, these actuator mechanisms are unwieldy and are not readily adaptable to be used in a stand-alone manner and a hand-held manner. Further, many of these actuator mechanisms exhibit a great deal of power consumption. Generally, valves having tilt-activated valve stems require less force for activation than valves having vertically activated valve stems. Release valves requiring smaller activation forces are advantageous because such valves require less power to actuate. Decreased power consumption will allow for longer power source life times. Smaller activation forces are also advantageous for automated activation because smaller required forces allow for simpler, smaller, and/or less costly automated designs.

Existing automated valve activation systems for valves having tilt-activated valve stems are complex and may be difficult to manufacture. Complex systems including precise interactions of a multitude of moving parts may also be expensive to manufacture and too large to fit in an overcap for a container. Complex systems may also require more power to operate and may have a greater tendency to break than systems of simpler construction.

SUMMARY OF THE INVENTION

According to one aspect of the invention, a volatile material dispenser includes a housing adapted to be releasably mounted on a container having a tilt-activated valve stem. The housing includes a discharge orifice. A drive unit is disposed within the housing, wherein the drive unit is activated in response to a signal from at least a sensor, and wherein the drive unit is adapted to radially displace the tilt-activated valve stem in response to the signal.

According to another aspect of the invention, an overcap for a volatile material container includes a housing adapted to be releasably mounted on a container having a tilt-activated valve stem. A displacement member is disposed within the housing, wherein a first end of the displacement member is adapted to be disposed on the tilt-activated valve stem and a second end is in fluid communication the first end. A flange extends radially from the displacement member. A drive unit is disposed within the housing, wherein the drive unit includes a camming member adapted to impinge the flange of the displacement member and radially displace the displacement member in response to an activation signal.

According to yet another aspect of the invention, a volatile material dispensing system includes a housing adapted to releasably hold a container having a tilt-activated valve stem. The housing is further adapted to retain a body of the container in a substantially stationary manner. A drive motor is disposed within the housing, wherein the drive motor is in mechanical communication with a cam that is adapted to radially displace the tilt-activated valve stem in response to a signal from at least a sensor.

BRIEF DESCRIPTION OF THE DRAWINGS

FIG. 2 is a front elevational view of the overcap of FIG. 1;

FIG. 3 is a rear elevational view of the overcap of FIG. 1;

FIG. 4 is a right side elevational view of the overcap of FIG. 1;

FIG. 5 is a left side elevational view of the overcap of FIG. 1;

Other aspects and advantages of the present invention will become apparent upon consideration of the following detailed description, wherein similar structures have similar reference numerals.

DETAILED DESCRIPTION OF THE DRAWINGS

Figure 1:
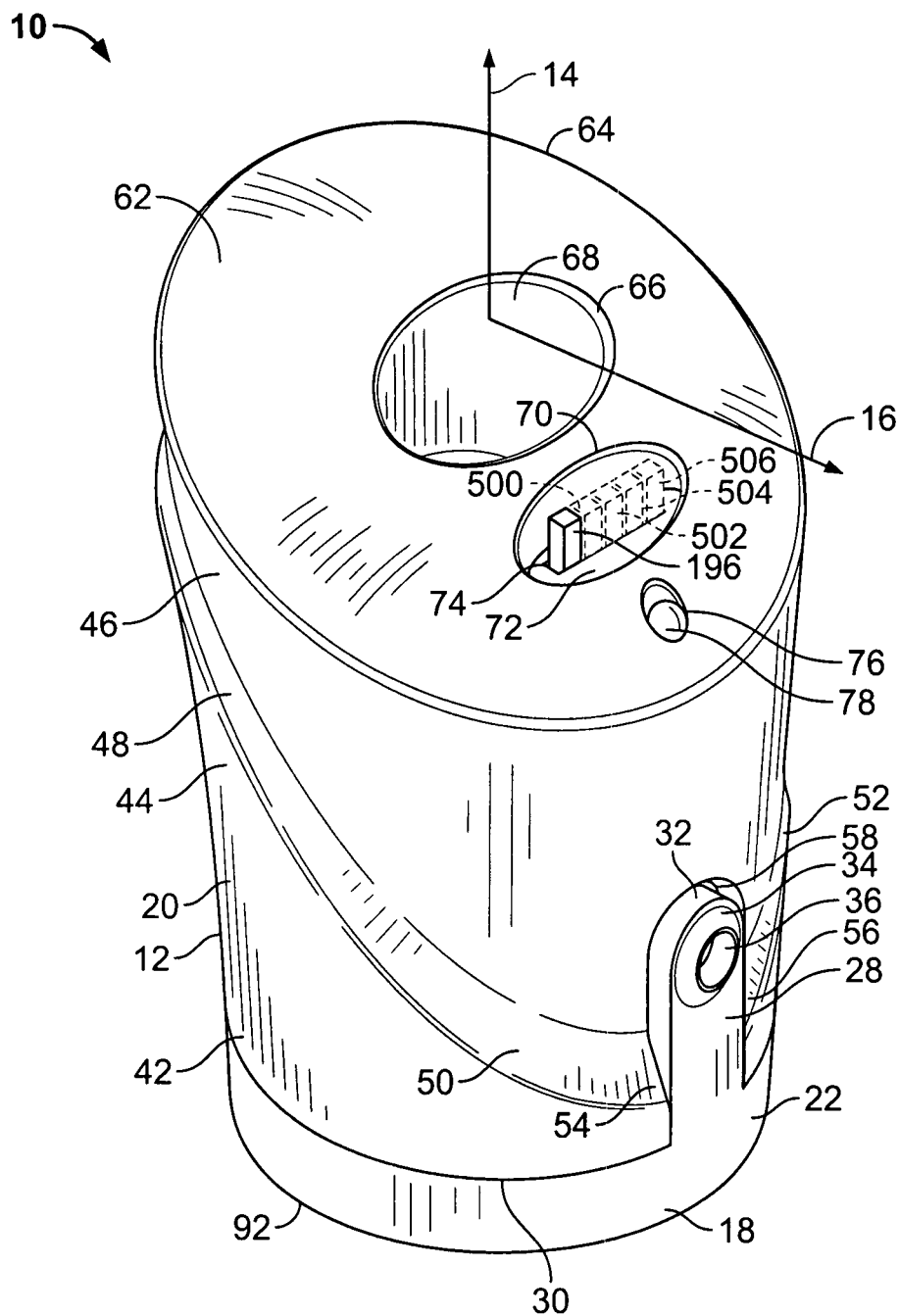
FIG. 1 is an isometric view of one embodiment of an actuator overcap.
Figure 6:
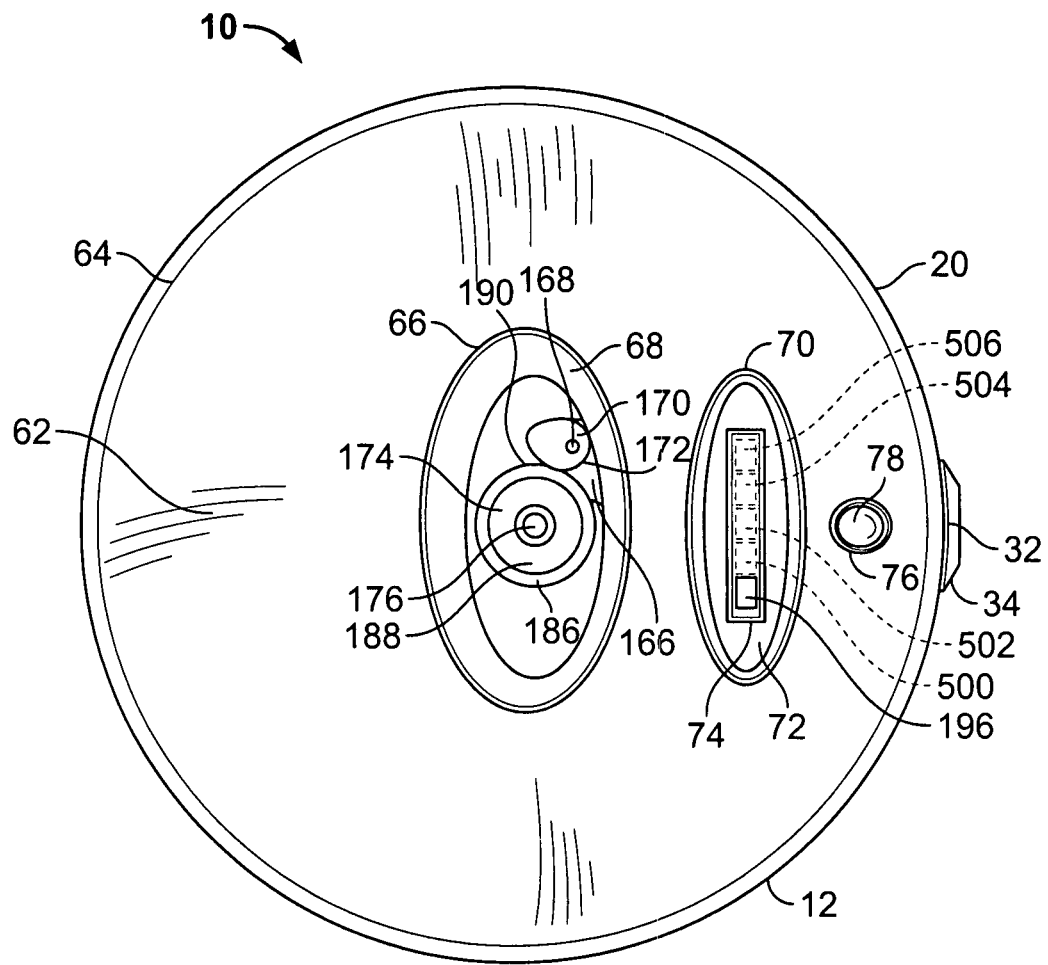
FIG. 6 is a top plan view of the overcap of FIG. 1.
Figure 7:
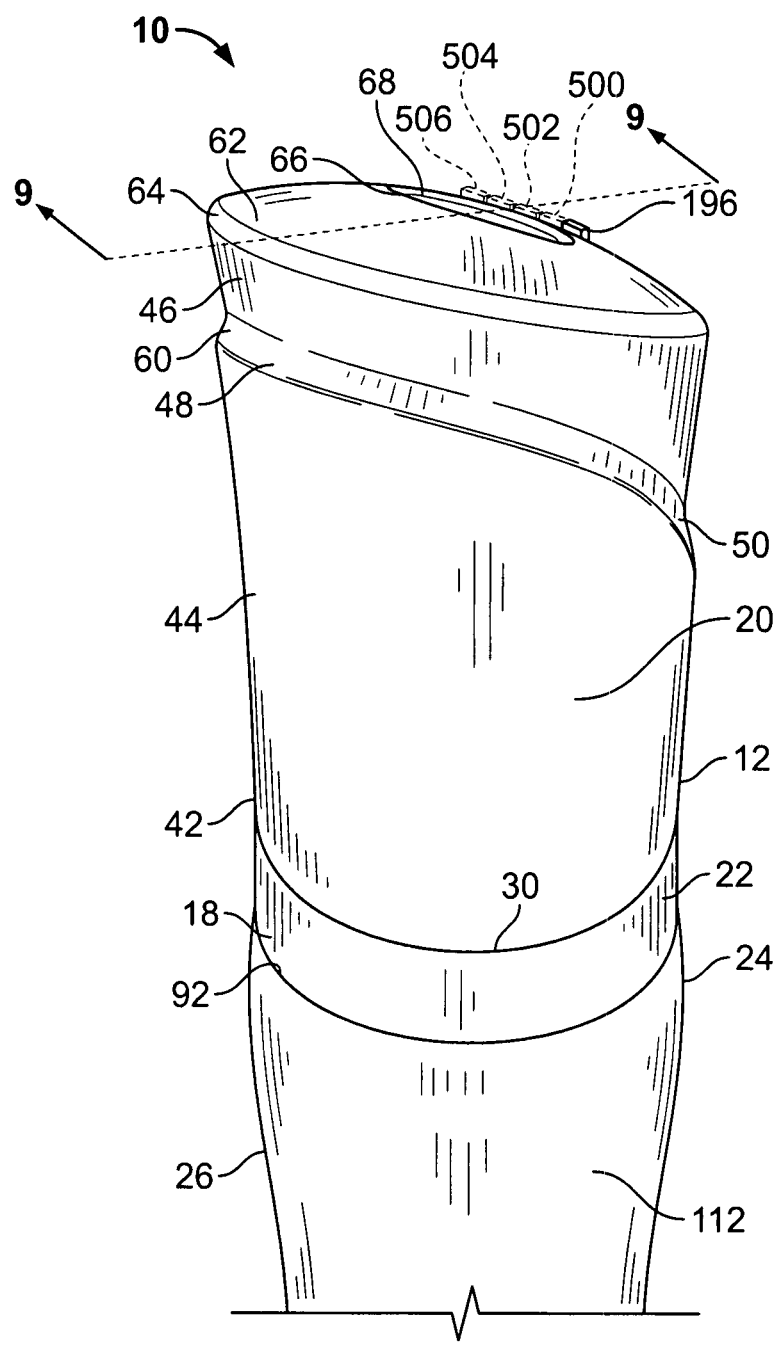
FIG. 7 is an isometric view of the overcap of FIG. 1 mounted on a fluid container.
Figure 8:
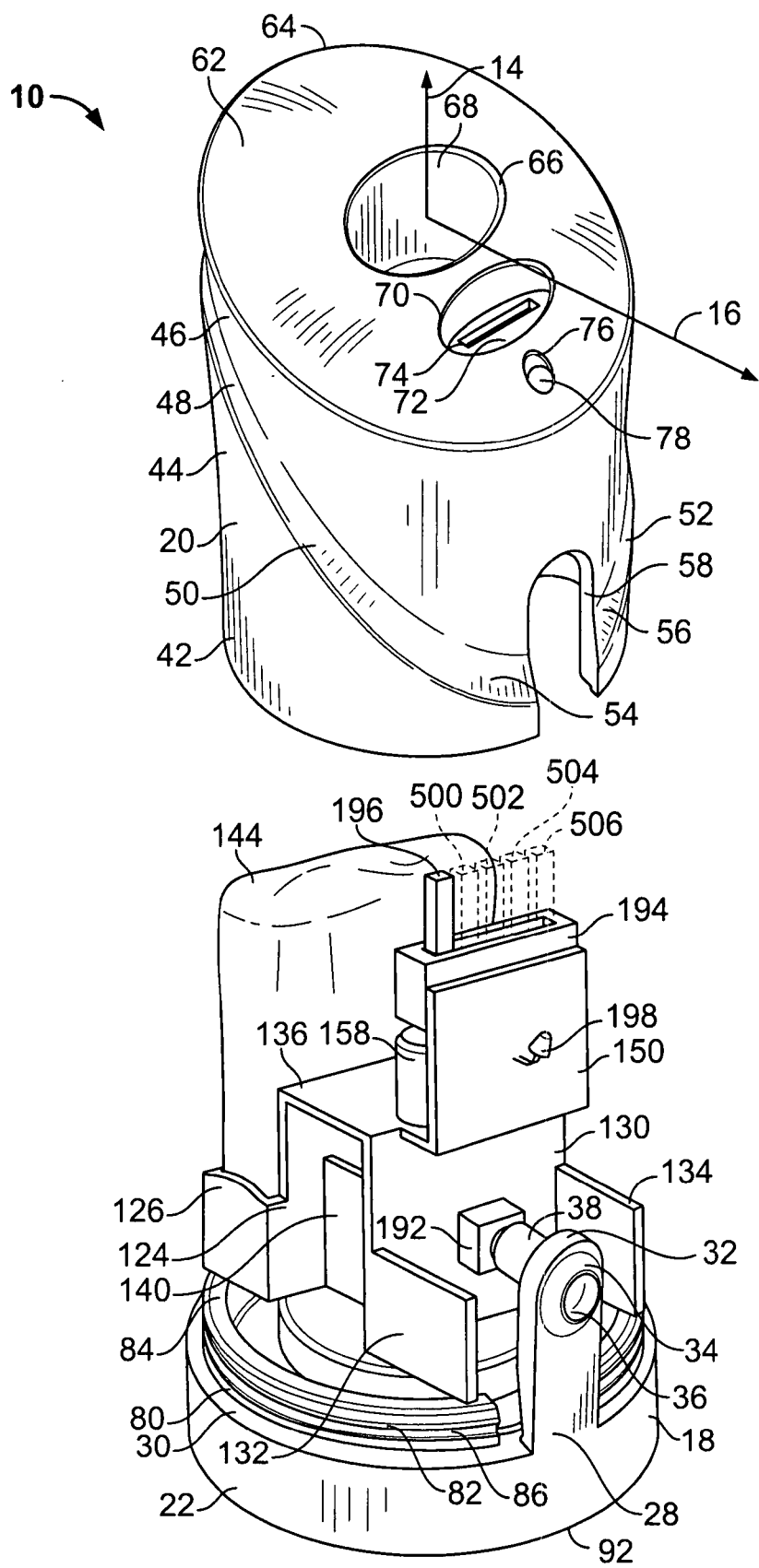
FIG. 8 is an exploded isometric view of the overcap of FIG. 1.

FIGS. 1-6 depict an actuator overcap 10 having a generally cylindrical housing 12 that has a longitudinal dimension along a longitudinal axis 14 and a radial dimension along a radial axis 16. The housing 12 includes a base portion 18 and a removable cap 20. The base portion 18 comprises a cylindrical section 22 adapted to be retained on an upper end 24 of a conventional aerosol container 26, which is shown in FIG. 7, and will be described in further detail below. A post 28 extends upwardly from a top end 30 of the cylindrical section 22. The post 28 includes a curved distal end 32 with an oval pushbutton 34 on an outer wall thereof. The pushbutton 34 is further provided with a concave depression 36. A cylindrical rod 38 (see FIG. 8) is provided on an inner wall 40 (see FIG. 9) of the post 28 generally opposite the pushbutton 34.

Referring again to FIGS. 1-6, the removable cap 20 includes a cylindrical bottom portion 42, which has a diameter substantially equal to that of the top end 30 of the cylindrical section 22. A sidewall 44 extends between the bottom portion 42 of the removable cap 20 and a top portion 46 thereof. The sidewall 44 tapers outwardly about the longitudinal axis 14 of the removable cap 20 so that a cross-sectional diameter of the removable cap adjacent the bottom portion 42 is smaller than a cross-sectional diameter of the removable cap 20 adjacent the top portion 46. The uniform tapering of the removable cap 20 is truncated by a stepped portion 48. The stepped portion 48 includes first and second tapered surfaces 50, 52, respectively, that extend inwardly toward the longitudinal axis 14 of the removable cap 20. The first and second tapered surfaces 50, 52 include first ends 54, 56, respectively, disposed on opposing sides of a groove 58 adjacent the bottom portion 42 of the removable cap 20. The tapered surfaces 50, 52, curve upwardly from the first ends 54, 56 toward a portion 60 of the removable cap 20 opposite the groove 58 and adjacent the top portion 46.

An upper surface 62 of the removable cap 20 is convex and is bounded by a circular peripheral edge 64. An elliptical shaped discharge orifice 66 is centrally disposed within the upper surface 62. A frusto-conical wall 68 depends downwardly into an interior of the removable cap 20 about a periphery of the discharge orifice 66. A curved groove 70 is disposed between the discharge orifice 66 and the peripheral edge 64. The groove 70 includes a flat bottom 72 with a rectangular notch 74 disposed therein. An aperture 76 is also provided between the groove 70 and the peripheral edge 64. A light transmissive rod 78 is held within the aperture 76 by an interference fit.

Figure 9:
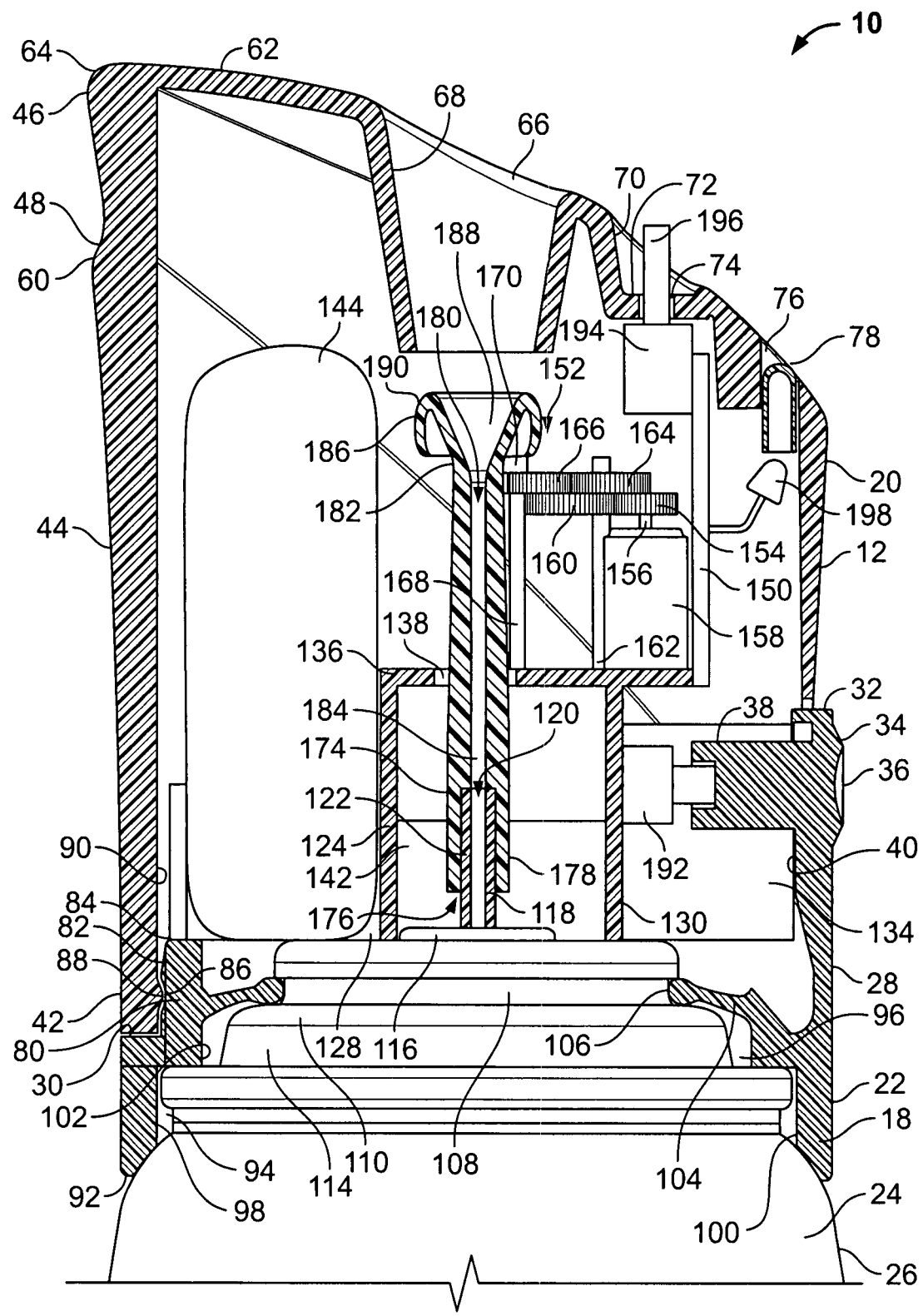
FIG. 9 is an enlarged partial sectional view taken generally along the lines 9-9 of FIG. 7.
Figure 10:
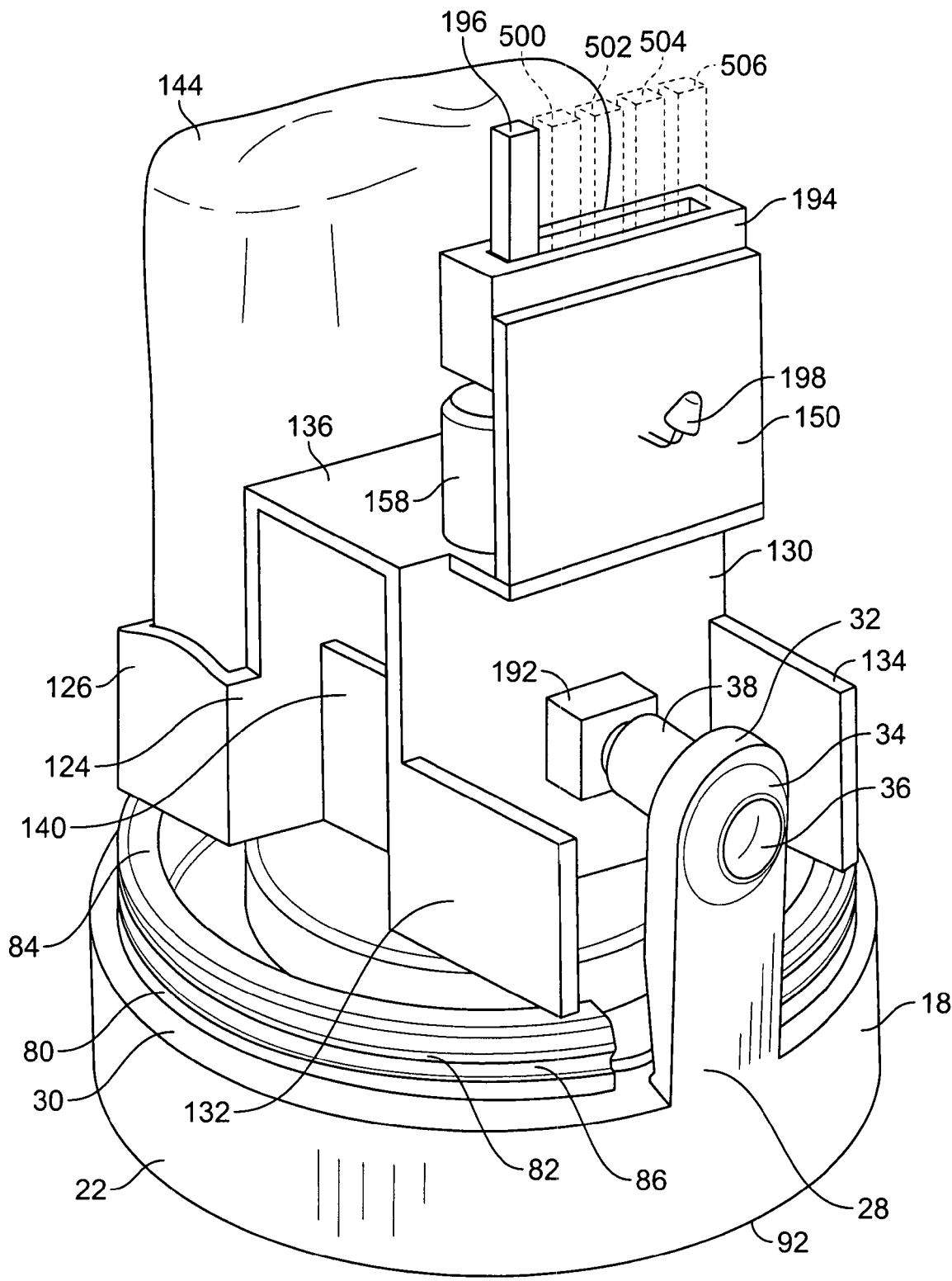
FIG. 10 is an isometric view of the overcap of FIG. 1 with a portion of a housing removed.

As shown in FIGS. 8-12, the base portion 18 includes a platform 80 that is disposed on the top end 30 of the cylindrical section 22. The platform 80 is sized to frictionally engage with the bottom portion 42 of the removable cap 20 when the removable cap is attached to the base portion 18. FIG. 9 illustrates that the platform 80 comprises an inwardly stepped portion, which includes a sidewall 82 and a top portion 84. The sidewall 82 includes a circumferential notch 86 adapted to fittingly receive an annular portion 88 on an inner wall 90 of the removable cap 20 adjacent the bottom portion 42 thereof. Further, additional retention support is provided by the groove 58, which is sized to fittingly receive the post 28 when the removable cap 20 is placed on the base portion 18. During the placement of the removable cap 20 on the section 22, the user aligns the groove 58 with the post 28 and slides the removable cap 20 downwardly until same contacts the top end 30 of the base portion 18 and forms an interference fit with the platform 80.

A bottom end 92 of the base portion 18 is also shaped to fit on the upper end 24 of the aerosol container 26. FIG. 9 shows that the present embodiment includes recesses 94, 96 around an inner circumference 98 of the base portion 18. The recess 94 is defined by a surface 100 and the recess 96 is defined by a surface 102, which includes an annular portion 104 that projects inwardly therefrom. A distal end 106 of the annular portion 104 forms a snap fit with an undercut 108 of a mounting cup 110. The surface 100 forms an interference fit with portions of the aerosol container 26 beneath the mounting cup 110. The snap fit between the annular portion 104 and the undercut 108 and the interference fit between the surface 100 and portions of the aerosol container 26 assist in securely mounting the base portion 18 to the aerosol container 26. Further, contact between the bottom end 92 of the base portion 18 and the upper end 24 of the aerosol container 26 may assist in preventing rocking or shifting of the base portion 18 when mounted on the aerosol container 26.

In another embodiment of the overcap 10, the removable cap 20 and the base portion 18 form an integral unit that is attached to the upper end 24 of the aerosol container 26 by an interference fit. Indeed, regardless of whether the housing 12 comprises one or more components, the housing 12 may be retained on the aerosol container 26 in any manner known by those skilled in the art. For example, the overcap retention structures described in Balfanz U.S. Pat. No. 4,133,408, Demarest U.S. Pat. No. 5,027,982, Demarest et al. U.S. Pat. No. 5,609,605, and Helf et al. U.S. patent application Ser. No. 11/712,548, filed on May 10, 2007, which are herein incorporated by reference in their entirety, may be used in connection with any of the embodiments described herein. Further, any of the aesthetic aspects of the overcap 10 described herein may be modified in any manner known by one skilled in the art, e.g., the stepped portion 48 could be removed or the housing 12 could be provided with a different shape.

The overcap 10 discharges fluid from the aerosol container 26 upon the occurrence of a particular condition. The condition could be the manual activation of the overcap 10 or the automatic activation of the overcap 10 in response to an electrical signal from a timer or a sensor. The fluid discharged may be a fragrance or insecticide disposed within a carrier liquid, a deodorizing liquid, or the like. The fluid may also comprise other actives, such as sanitizers, air fresheners, odor eliminators, mold or mildew inhibitors, insect repellents, and/or the like, and/or that have aromatherapeutic properties. The fluid alternatively comprises any fluid known to those skilled in the art that may be dispensed from a container. The overcap 10 is therefore adapted to dispense any number of different fluid formulations.

Still referring to FIG. 9, the container 26 may be an aerosol container of any size and volume known to those skilled in the art. However, the container 26 preferably comprises a body 112 (see FIG. 7) with the mounting cup 110 crimped to the upper end 24 thereof. The mounting cup 110 is generally cylindrical in shape and includes an outer wall 114 that extends circumferentially therearound (see FIG. 9). A pedestal 116 extends upwardly from the mounting cup 110. A valve assembly (not shown) within the container 26 includes a valve stem 118 extending upwardly from the pedestal 116. A bore 120 extends from the valve assembly through the valve stem 118. The valve stem 118 is of the tilt-activated type similar to the one described in Van der Heijden U.S. Pat. No. 4,064,782, which is herein incorporated by reference in its entirety.

When the valve stem 118 is tilted radially to a sufficient degree, i.e., into an operable position, the valve assembly is opened and the contents of the container 26 are discharged from a discharge end 122 of the valve stem 118. In the terminology of the axisymmetric coordinate system used herein, a radial displacement includes any displacement of the discharge end 122 of the valve stem 118 away from the longitudinal axis 14. Such a radial displacement may therefore be characterized as a lateral or a transverse displacement of the discharge end 122 of the valve stem 118. The contents of the container 26 may be discharged in a continuous or metered dose. Further, the discharging of the contents of the container 26 may be effected in any number of ways, e.g., a discharge may comprise a partial metered dose or multiple consecutive discharges.

Referring to FIGS. 8-12, a first transverse wall 124 is provided with first and second frame members 126, 128 on opposing sides thereof. The first and second frame members 126, 128 are attached to the top portion 84 of the platform 80. A second transverse wall 130 is provided with third and fourth frame members 132, 134 that extend from opposing sides thereof and that are similarly attached to the top portion 84 of the platform 80. A horizontal platform 136 spans the first and second transverse walls 124, 130 and includes an aperture 138 (see FIG. 9) disposed therethrough. Third and fourth transverse walls 140, 142 are also provided to add rigidity to the structure of the base 18.

Figure 13:
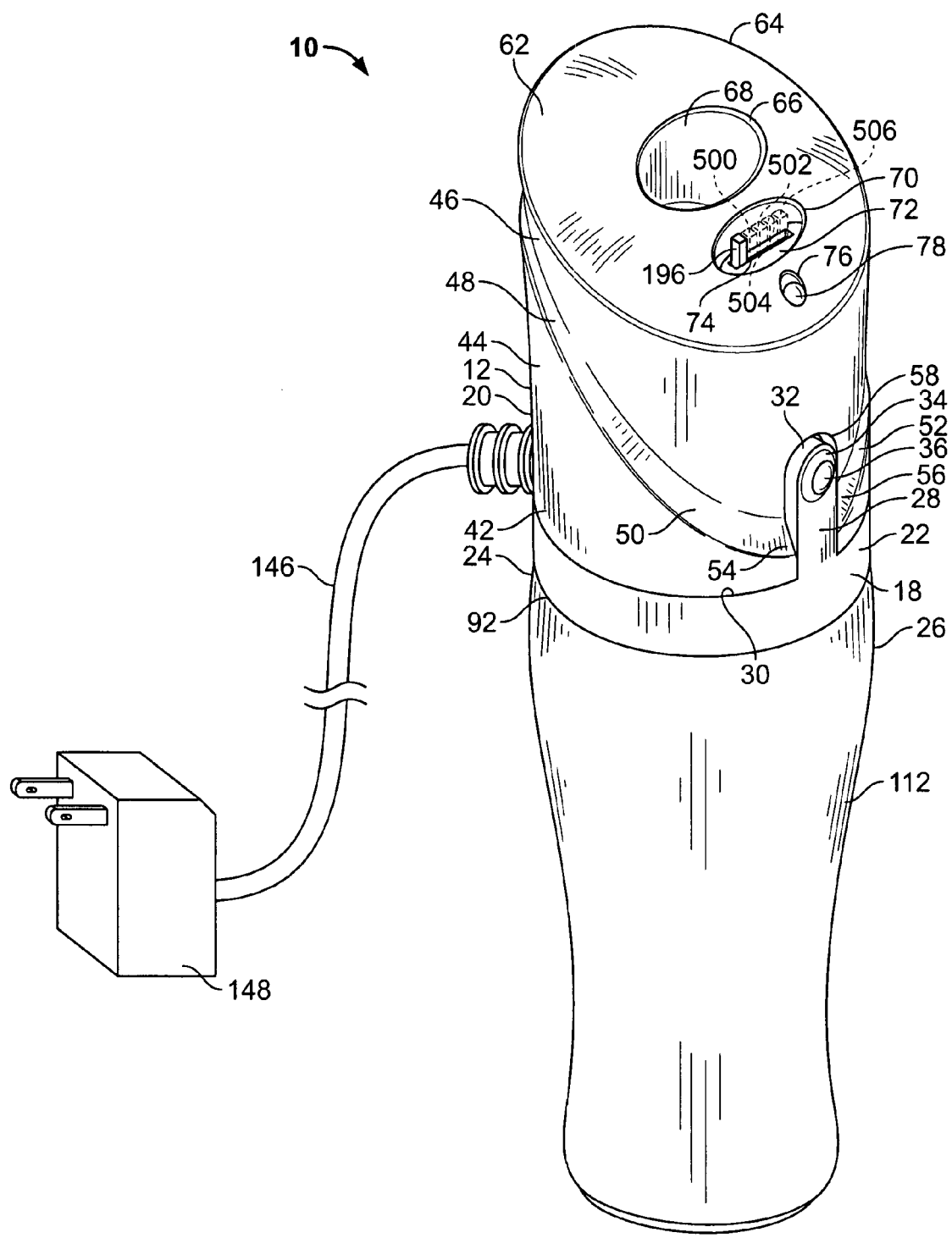
FIG. 13 is another embodiment of an overcap similar to the one depicted in FIG. 7, which includes an A.C. power connector.

The first and second frame members 126, 128 are adapted to retain a D.C. power source 144 comprising one or more AA or AAA batteries therein. The power source 144 of the present embodiment is shown schematically to illustrate the interchangeability of the batteries with other power sources. In some embodiments, the batteries may be replaced by a rechargeable Nickel-Cadmium battery pack having an electrical lead 146 that may be used to connect the battery pack to an A.C. power outlet 148, such as seen in FIG. 13. In another embodiment, the D.C. power source 144 may be entirely replaced by an A.C. power adapter having an appropriate power transformer and A.C./D.C. converter as known to those of skill in the art.

Figure 11:
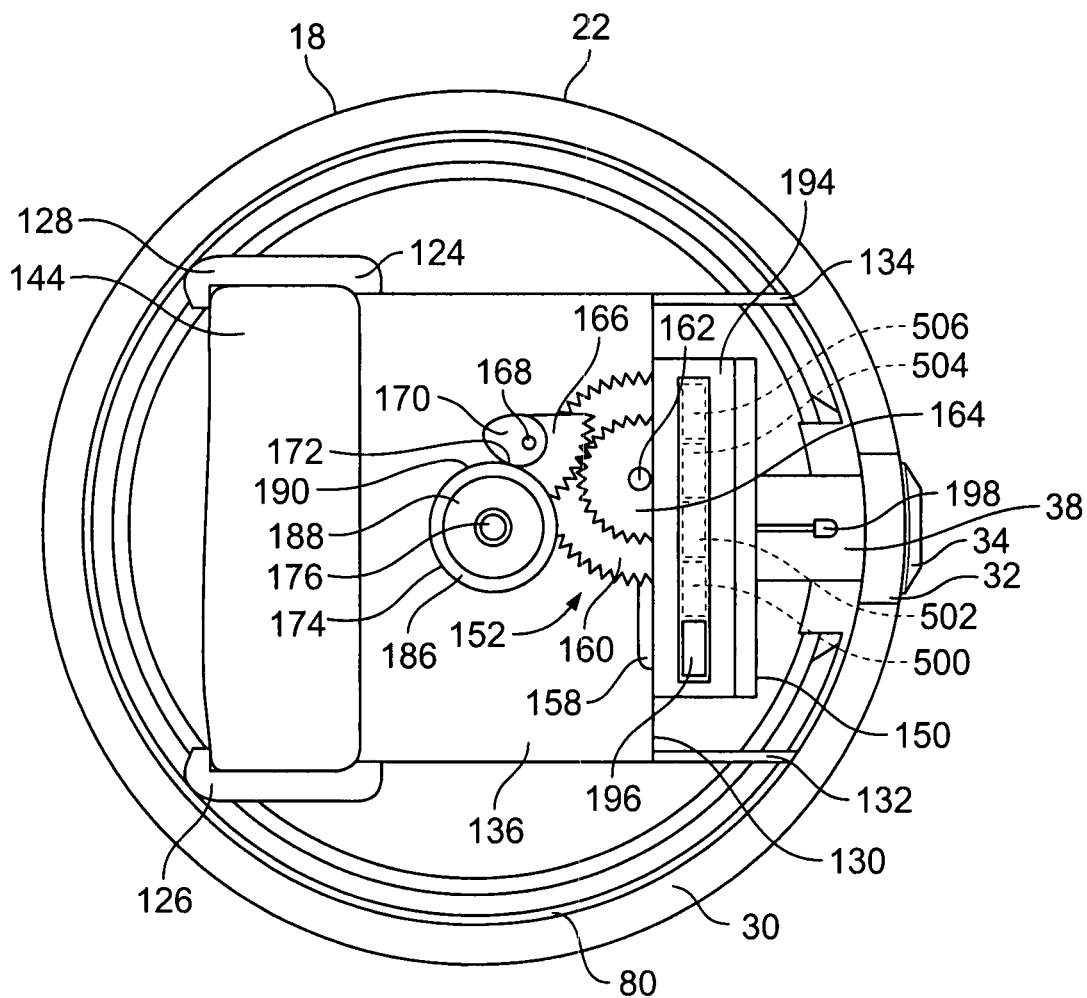
FIG. 11 is a top plan view of the overcap of FIG. 10.
Figure 12:
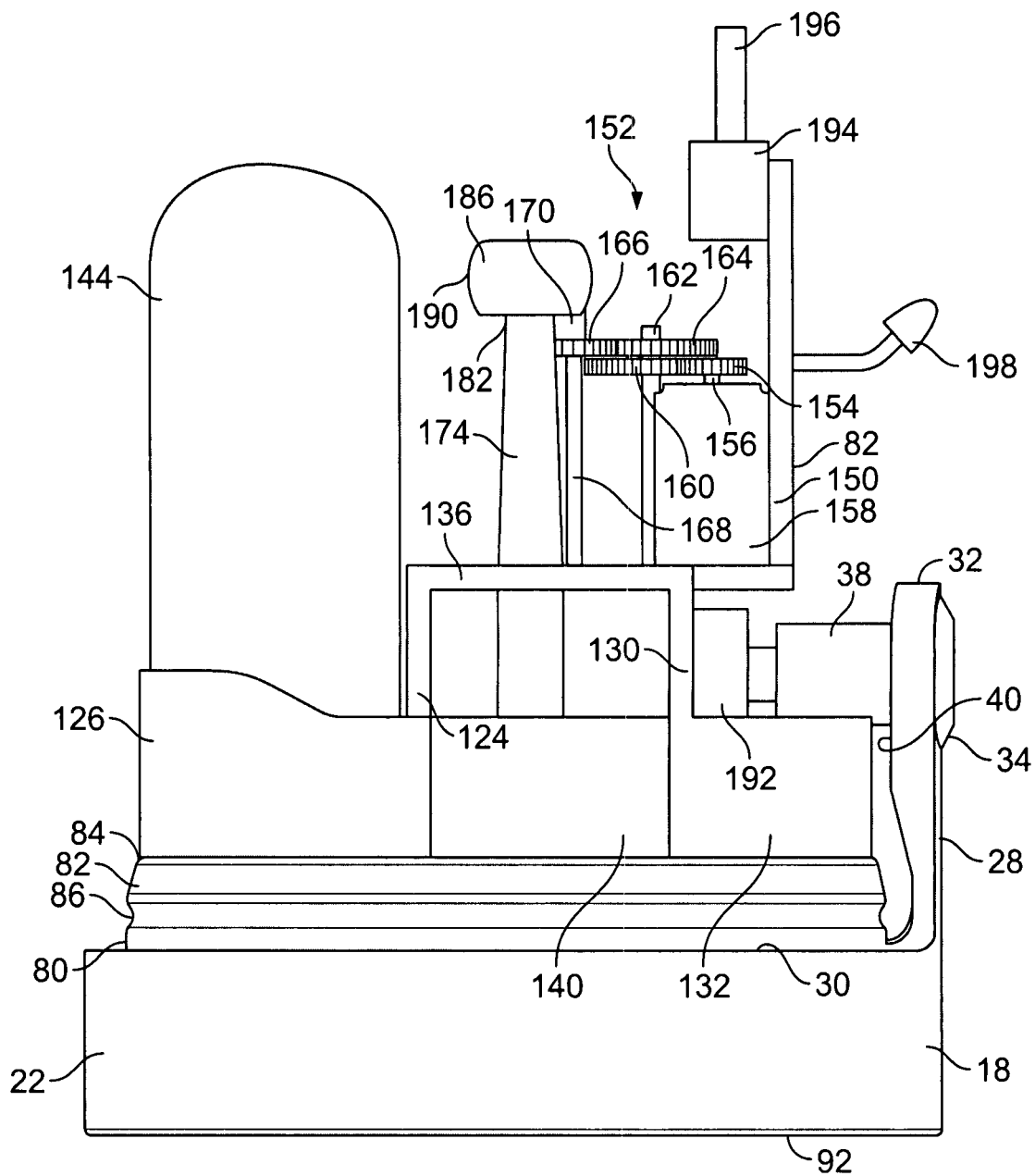
FIG. 12 is a side elevational view of the overcap of FIG. 10.

In the present embodiment, a control circuit (not shown) is etched on a printed circuit board 150. The control circuit allows for the electrical activation of a drive unit 152 disposed within the housing 12 (see FIGS. 9, 11, and 12). The drive unit 152 includes a main drive gear 154 that is mounted on a rotatable drive shaft 156 of an electric motor 158. The main drive gear 154 is in mechanical association with a first transfer gear 160 that is fixedly mounted on a first transfer shaft 162. A smaller second transfer gear 164 is also fixedly mounted on the first transfer shaft 162. The first transfer shaft 162 is rotatably mounted to the platform 136. A third transfer gear, e.g., a butterfly gear 166, is in mechanical association with the second transfer gear 164. The butterfly gear 166 is fixedly mounted on a second transfer shaft 168 that is similarly mounted to the platform 136 in a rotatable manner. A cam or camming member, such as an actuating cam 170 shown in FIGS. 9, 11, and 12, is provided on the butterfly gear 166. The actuating cam 170 includes a lateral surface 172 having a generally arcuate shape (see FIGS. 6 and 11).

A displacement member 174 is shown in cross-section in FIG. 9. The displacement member 174 includes an opening 176 at a first end or attachment end 178 thereof. The attachment end 178 is press fit or otherwise attached to the valve stem 118 in a manner that allows the opening 176 to be in fluid communication with the bore 120 of the valve stem 118. Further, the attachment end 178 is fashioned in a manner to provide for a substantially fluid tight seal between an outer portion of the valve stem 118 and the displacement member 174. An aperture 180 is provided adjacent a second end or distal end 182 of the displacement member 174, which is in fluid communication with the opening 176 by a conduit 184. A dispensing nozzle 186 is provided at the distal end 182 of the displacement member 174. In the present embodiment, the dispensing nozzle 186 includes a discharge conduit 188 having an outwardly tapering cross-section in fluid communication with the aperture 180. The dispensing nozzle 186 also includes a contoured outer surface 190 that is wider than other portions of the displacement member 174, which is adapted to be impinged laterally by the surface 172 of the actuating cam 170. In other embodiments, the outer surface 190 includes a different shape, a different size, or is removed altogether, insofar as the displacement member 174 may be impinged by the actuating cam 170. In yet a different embodiment, the discharge conduit 188 of the dispensing nozzle 186 is modified to have a different shape, e.g., the walls defining the discharge conduit 188 could taper inwardly, could be provided with protrusions, or could be coextensive with the conduit 184. In still a different embodiment, the conduit 184 is modified to have a different shape and/or to have a varying cross-sectional shape.

Turning again to FIGS. 9, 11, and 12, the actuating cam 170 is shown to be disposed adjacent the dispensing nozzle 186. In a non-actuation position, i.e., when the motor 158 is not activated, the lateral surface 172 of the actuating cam 170 is positioned out of contact with the outer surface 190 of the dispensing nozzle 186 or in contact to a degree insufficient to radially tilt the dispensing member 174 to actuate the valve stem 118. During an operation sequence, the motor 158 is activated to transfer power through the main drive gear 154, the first and second transfer gears 160, 164, the butterfly gear 166, and through the actuating cam 170. In the present embodiment, a quarter turn of the actuating cam 170 results in the surface 172 of the actuating cam 170 impinging against the outer surface 190 of the displacement member 174 and displacing same radially. For purposes of the present embodiment, this level of displacement is sufficient to radially tilt the valve stem 118 a sufficient degree to open the valve assembly within the container 26. The first and second transfer gears 160, 164, the butterfly gear 166, and the actuating cam 170 are sized to allow for precise control of the rotational displacement of the actuating cam 170. One skilled in the art will know how to modify the above-noted structure to effect a full or partial radial translation of the displacement member 174 and/or the valve stem 118 during an operational sequence.

FIGS. 8-10 and 12 depict a normally open switch 192 disposed on the second transverse wall 130 that is in electrical communication with the printed circuit board 150. The switch 192 is operably aligned with the pushbutton 34 such that the manual depression of the pushbutton 34 closes the open switch 192. Closing the switch 192 causes the activation of the electric motor 158 in a similar manner as discussed above. Further, a user selectable switch assembly 194 is disposed adjacent a top portion of the printed circuit board 150. The user selectable switch assembly 194 of the present embodiment is a linear displacement type switch having a control member, e.g., a finger 196, extending upwardly therefrom. The finger 196 may be used to select different operating modes (as discussed in greater detail below). The finger 196 fits within the notch 74 when the removable cap 20 is engaged with the base portion 18 such that a user may operatively interact with the finger 196 (see FIG. 1). In different embodiments, the user selectable switch assembly 194 may be rotational and controlled by a turning knob, or could have any other geometric configuration and corresponding control mechanism as is known in the art. Further, a light emitting diode (LED) 198 is disposed on the printed circuit board 150 adjacent the light transmissive rod 78 of the removable cap 20 (see FIG. 9).

Figure 14:
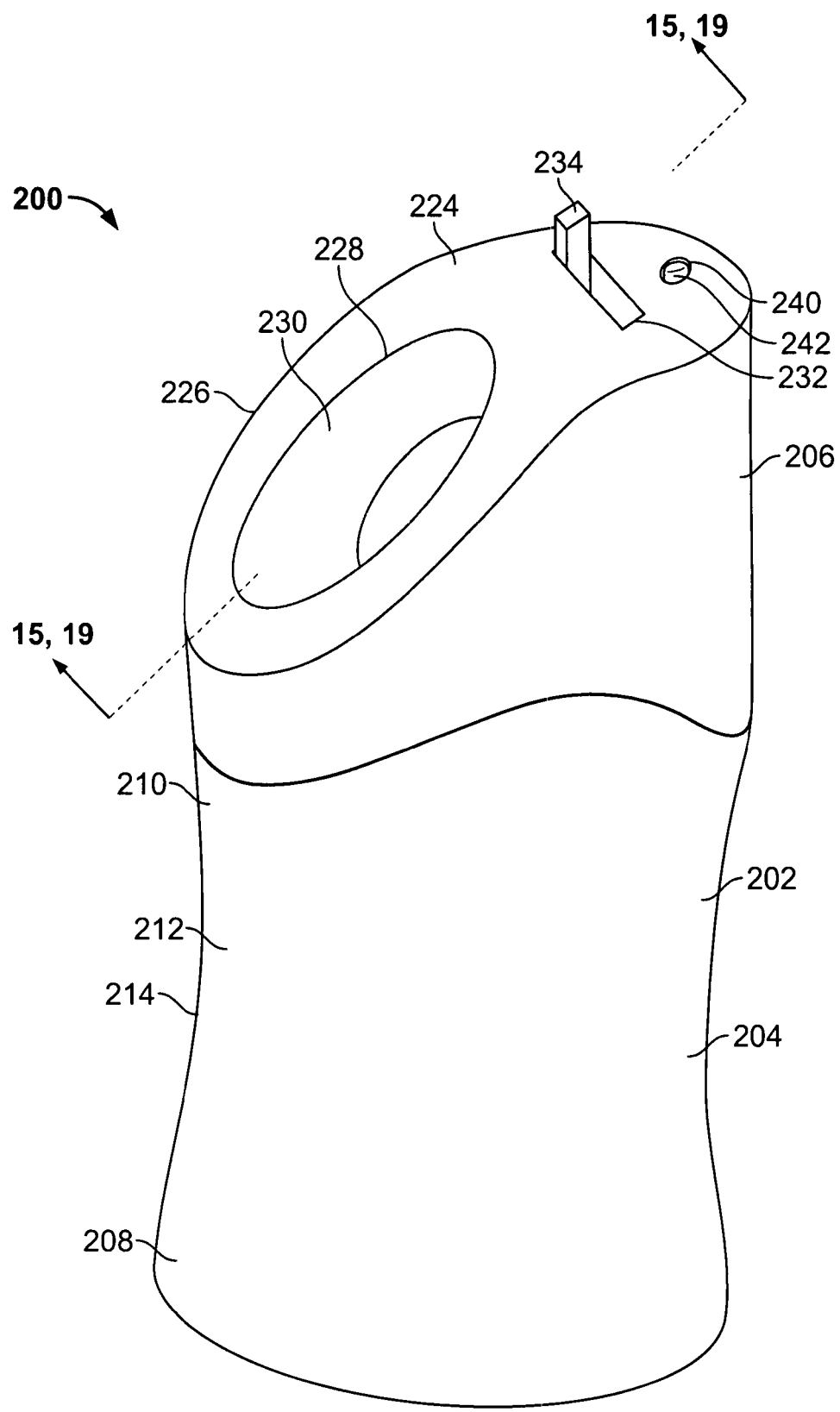
FIG. 14 is an isometric view of another embodiment of a dispensing system.
Figure 15:
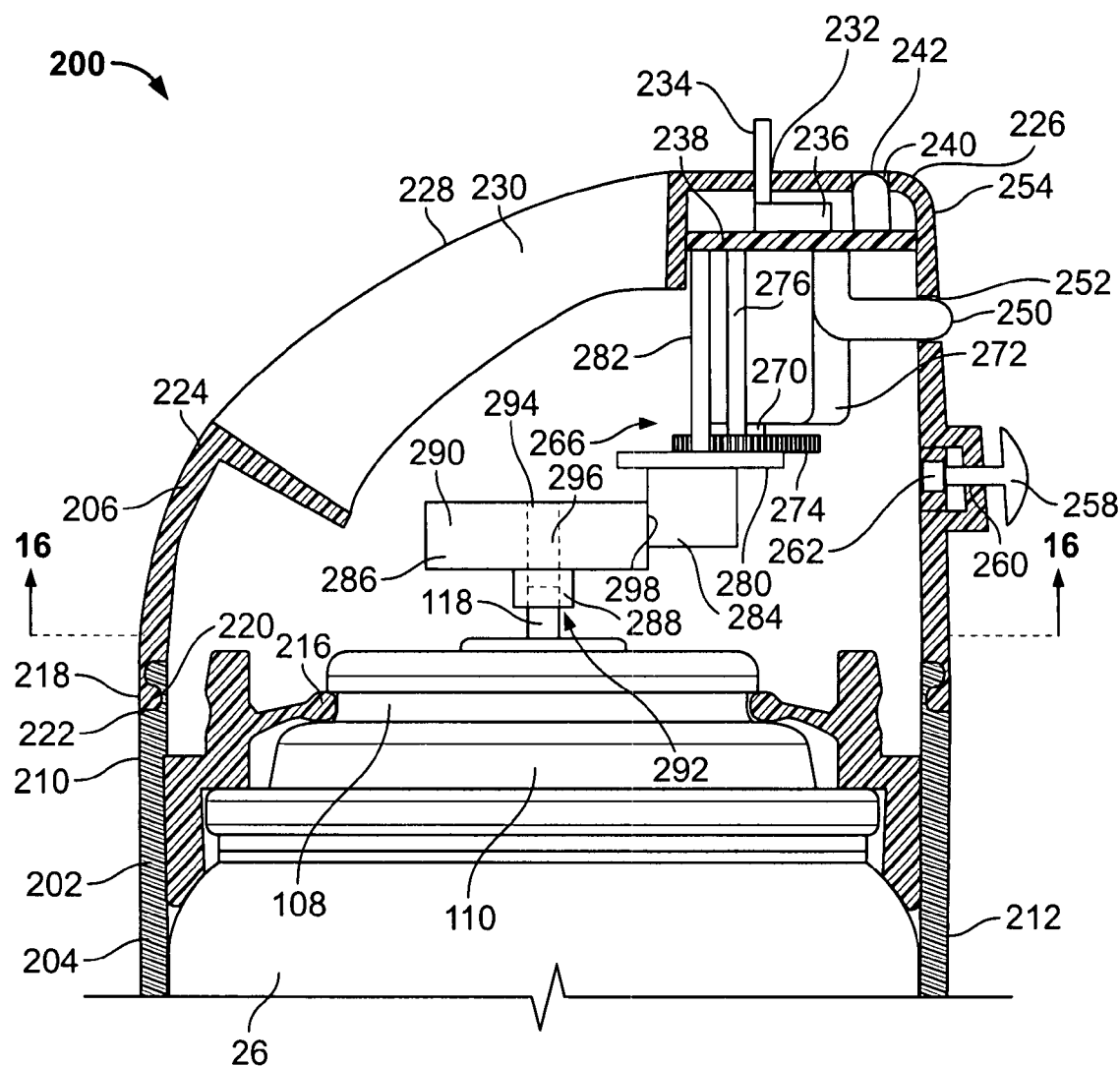
FIG. 15 is a partial sectional view taken generally along the lines 15-15 of FIG. 14, with portions of the system behind the plane of section removed for purposes of clarity.
Figure 16:
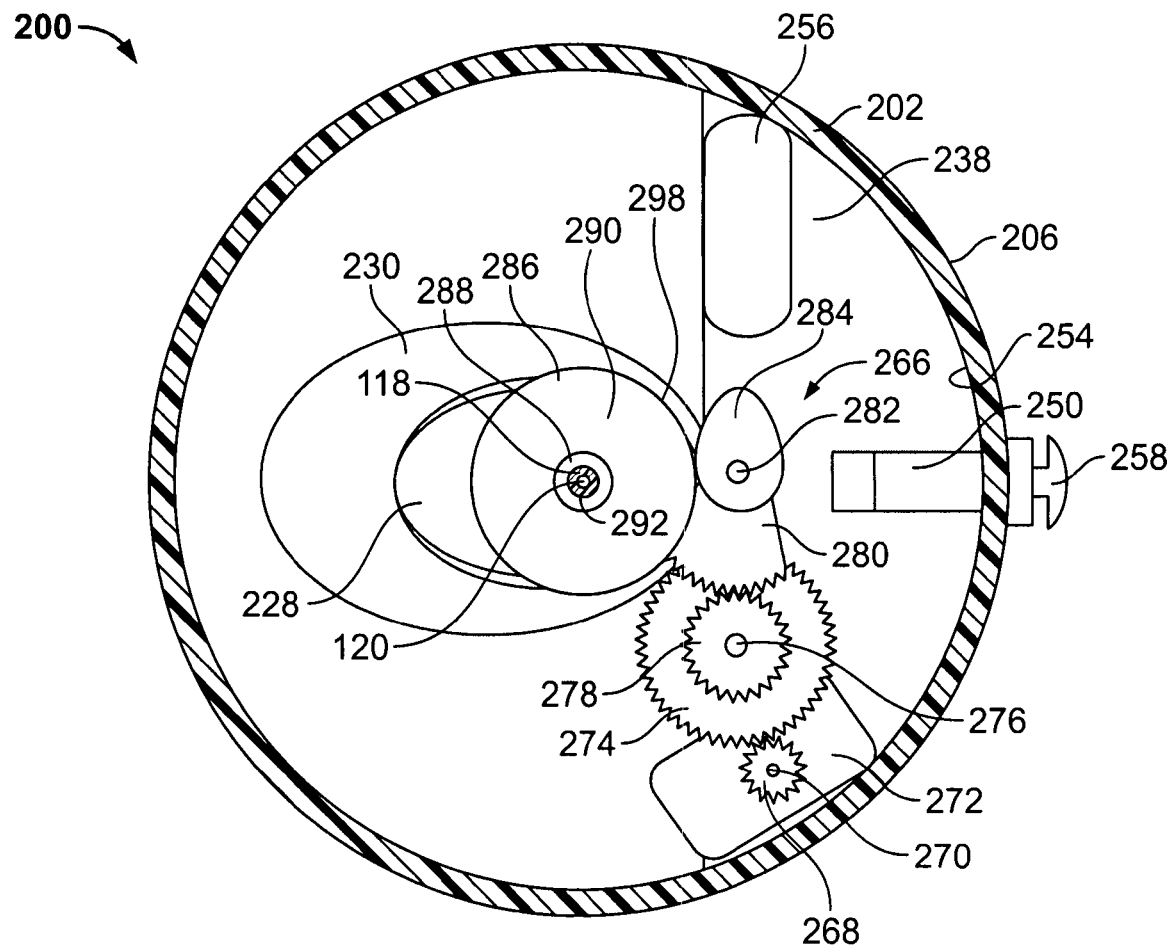
FIG. 16 is a sectional view taken generally along the lines 16-16 of FIG. 15.

FIGS. 14-16 depict a different embodiment of a dispensing system 200, which comprises a housing 202 having a base 204 and a removable top 206. The base 202 includes a lower end 208 and an upper end 210. A sidewall 212 having a varying cross-sectional diameter extends between the lower and upper ends 208, 210, so that a medial portion 214 of the sidewall has a smaller cross-section than the lower and upper ends 208, 210. The container 26 is retained within the base 204 of the housing 202 in a substantially immovable manner. In the present embodiment, a plurality of annular protrusions 216 snap-fittingly engage with the undercut 108 of the mounting cup 110 of the aerosol container 26. However, it is envisioned that the container 26 may be retained within the housing 202 in any manner known to those skilled in the art and/or discussed herein, e.g., a bottom end of the container 26 could be held within a fitted circular recess in the lower end 208 of the base 204 or the container 26 could be held by an interference fit between interior portions of the housing 202 and portions of the container 26.

The removable top 206 is adapted to be removably disposed on the upper end 210 of the base 204. In the present embodiment, a bottom edge 218 of the removable top 206 includes an inwardly extending annular protrusion 220 that snap fits into a corresponding annular groove 222 disposed within the upper end 210 of the base 204. Removal of the removable top 206 exposes an interior of the housing 202 and allows a user to insert the container 26 therein. The removable top 206 includes an upper surface 224 having a generally convex shape that is bounded by a curved peripheral edge 226. An elliptical shaped discharge orifice 228 is disposed within the upper surface 224. A frusto-conical wall 230 depends downwardly into an interior of the housing 202 about a periphery of the discharge orifice 228. A rectangular notch 232 is disposed between the discharge orifice 228 and the peripheral edge 226. A finger 234 extends upwardly through the rectangular notch 232 from a user selectable switch assembly 236 mounted to a platform 238 disposed within the interior of the housing 202. An aperture 240 is also provided between the rectangular notch 232 and the peripheral edge 226. An LED 242 is disposed on the platform 238 and extends upwardly through the aperture 240.

Turning to FIG. 15, the platform 238 of the present embodiment is shown with greater particularity. A sensor 250 is provided on a bottom side of the platform 238. A sensing portion of the sensor 250 is exposed to the environment through an opening 252 in the removable top 206 beneath the peripheral edge 226 thereof. The platform 238 extends between the frusto-conical wall 230 and a sidewall 254 of the removable top 206. A printed circuit board (not shown) is affixed to the platform 238 and is in electrical communication with the switch assembly 236, the LED 242, and the sensor 250. A power source 256 (see FIG. 16), similar to the power source 144 described above, is also provided adjacent the platform 238. Further, a spring-loaded pushbutton 258 is provided within an orifice 260 of the sidewall 254 beneath the sensor 250. The pushbutton 258 is operably aligned with a normally open switch 262, which is adapted to be closed upon manual depression of the pushbutton 258 by a user.

In the present embodiment, a control circuit (not shown) is etched on the printed circuit board. The control circuit allows for the electrical activation of a drive unit 266 disposed within the housing 202 (see FIGS. 15 and 16). The drive unit 266 is similar to the drive unit disclosed above in connection with FIGS. 9, 11, and 12. The drive unit 266 includes a main drive gear 268 fixedly mounted to a rotatable shaft 270 of an electric motor 272. The main drive gear 268 is in mechanical association with a first transfer gear 274 that is fixedly mounted to a first transfer shaft 276. A smaller second transfer gear 278 is also fixedly mounted on the first transfer shaft 276. The first transfer shaft 276 is rotatably mounted to the platform 238. A third transfer gear 280 is in mechanical association with the second transfer gear 278. The third transfer gear 280 is fixedly mounted on a second transfer shaft 282 that is similarly mounted to the platform 238 in a rotatable manner. An actuating cam 284 is also fixedly mounted on the second transfer shaft 282. Activation of the drive unit 266 causes a transfer of power from the electric motor 272, through the gear assembly (268, 278, 280), and to the actuating cam 284. The actuating cam 284 is disposed adjacent a displacement member 286, which may be similar in operation and structure as the displacement member 174 discussed above, to radially actuate the displacement member 286 and the valve stem 118 in response to an activation signal.

FIGS. 15 and 16 depict the displacement member 286 of the present embodiment with greater particularity. The displacement member 2136 comprises a stepped cylindrical member, wherein a lower portion 288 includes a cross-section smaller than that of an upper portion 290. The lower portion 288 includes an opening 292 for receipt of a distal end of the valve stem 118 in a similar manner as noted above. An aperture 294 is provided within the upper portion 290 of the displacement member 286, which is in fluid communication with the opening 292 by a conduit 296. An outer surface 298 of the upper portion 290 is disposed adjacent the actuating cam 284. When the drive unit 266 is activated, power is transferred through the first through third transfer gears 274, 278, 280, through the actuating cam 284, and into the upper portion 290. A quarter turn of the actuating cam 284, such as in a counter-clockwise direction from the position shown in FIG. 16, results in the radial displacement of the displacement member 286 a sufficient amount to tilt the valve stem 118 into an activation position, thereby opening the valve assembly within the container 26 to discharge a fluid therefrom. Any of the structural elements of the present embodiment may be modified in a similar manner as disclosed in connection with the other embodiments described herein.

Figure 17:
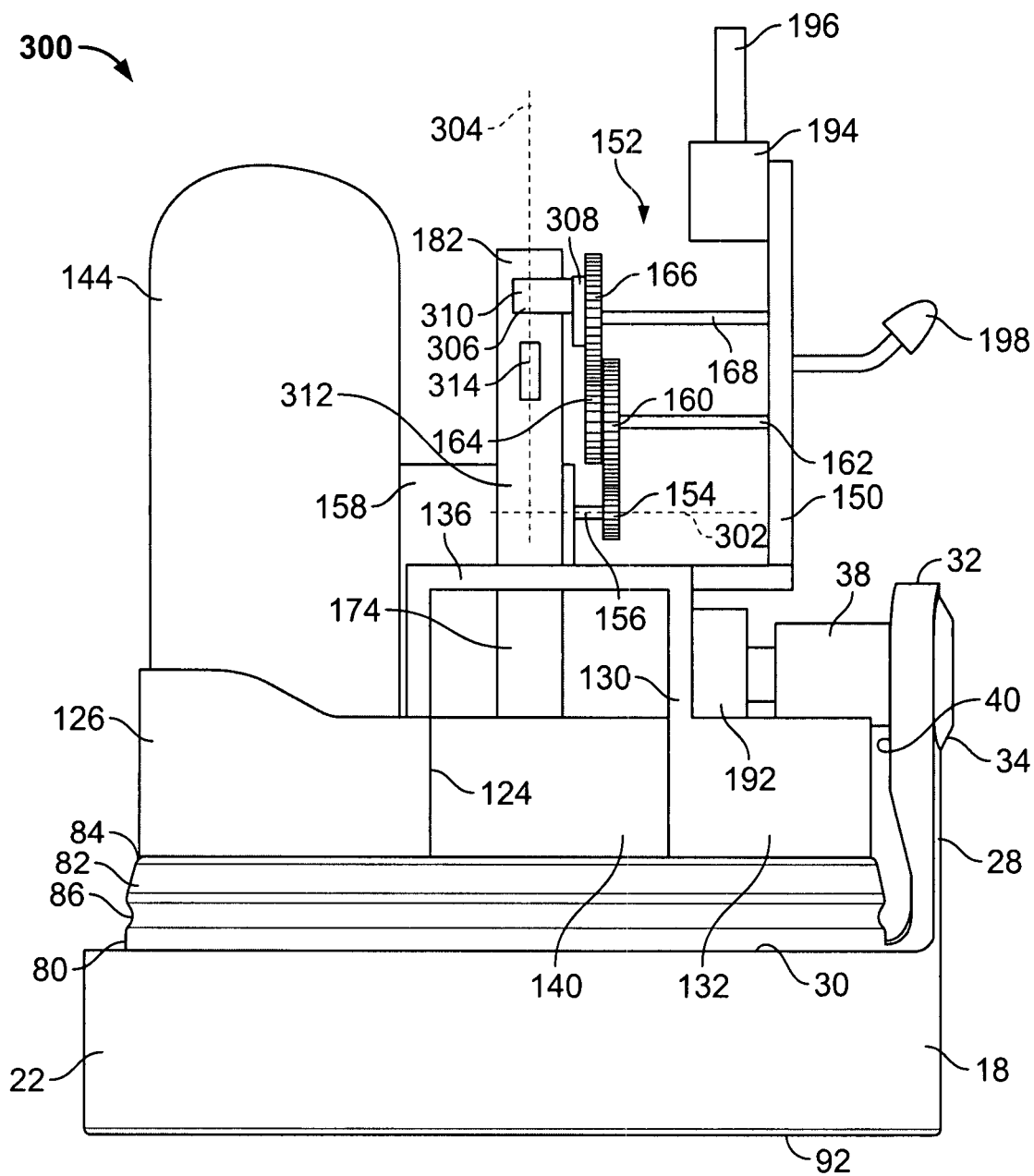
FIG. 17 is a side elevational view of yet another embodiment of an overcap, which is similar to the one shown in FIG. 12 except for a change to a drive unit and a displacement member.
Figure 18:
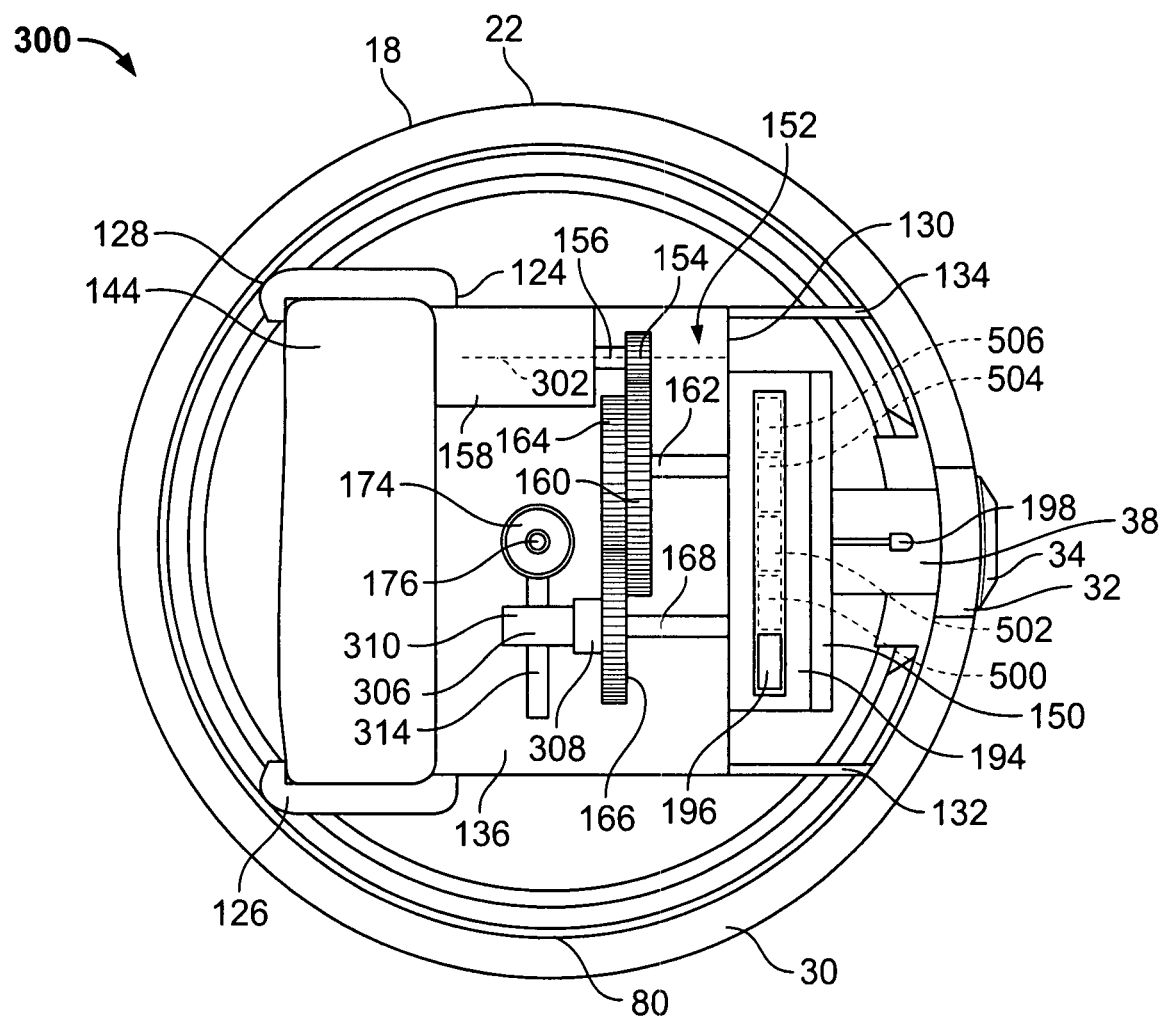
FIG. 18 is a top plan view of the overcap of FIG. 17.

FIGS. 17 and 18 depict another embodiment of an overcap 300 similar to the one depicted in FIGS. 8-12, which includes the drive unit 152 and the displacement member 174. However, in the present embodiment the electric motor 158 is mounted to the platform 80 in a manner that provides for a longitudinal axis 302 of the motor 158 to be substantially transverse to a longitudinal axis 304 of the displacement member 174. Similarly, the first and second transfer shafts 162, 168 of the present embodiment are mounted to the circuit board 150 in a substantially transverse manner with respect to the longitudinal axis 304 of the displacement member 174. The present embodiment is therefore illustrative of the various manners in which the elements of the drive unit 152 may be oriented to effect a lateral or radial displacement of the displacement member 174 and, consequently, the valve stem 118. For example, any of the one or more elements of the drive unit 152, i.e., the motor 158, the gears 154, 160, 164, 166, or the shafts 156, 162, 168, may be oriented in any position or angle radially about the longitudinal axis 302 of the displacement member 174 or a longitudinal axis of the valve stem 118, insofar as radial displacement of the displacement member 174 and the valve stem 118 may be effected. It is also contemplated that the drive unit 152 may comprise a set of transfer gears that are contained within a gear assembly having an input side driven by the motor 158 and an output side having an actuating cam attached thereto.

The present embodiment also includes an actuating cam 306, which is different than the actuating cam 170 of FIGS. 8-12. The actuating cam 306 comprises a base member 308 fixedly mounted to the second transfer shaft 168. A cam extension 310 is disposed on the base member 308 in a manner that is off-centered from the second transfer shaft 168 and a center of the third transfer gear 166. The third transfer gear 166 of the present embodiment is larger than the second transfer gear 164. In an alternative embodiment, the cam extension 310 may be disposed directly on the third gear 166 in an off-centered manner. The cam extension 310 of the present embodiment is generally cylindrical in shape, however, it is contemplated that other embodiments may use variously shaped or sized camming surfaces.

The displacement member 174 of the present embodiments has also been modified with respect to the displacement member 174 shown in FIGS. 8-12. FIGS. 17 and 18 show that the dispensing nozzle 186 has been removed from the distal end 182 of the displacement member 174. Instead, the displacement member 174 comprises a substantially uniformly cylindrical section 312, wherein the aperture 180 discharges the fluid into the atmosphere and/or through the overcap 300. A rectangular flange 314 extends substantially transversely from the section 312 with respect to the longitudinal axis 302 of the displacement member 174. It is also anticipated that the flange 314 may extend radially in any other manner with respect to the longitudinal axis 302 and that the flange 314 may comprise any other shape. In a non-actuation position, the cam extension 310 is positioned out of contact with the flange 314 or in contact to a degree insufficient to radially tilt the dispensing member 174 to actuate the valve stem 118.

During an operational sequence of the overcap 300, the motor 158 is activated to transfer power to the cam extension 310 in a similar manner as discussed above. In the present embodiment, rotation of the third gear 166 causes the cam extension to similarly rotate and impinge against a length of the flange 314. Impingement of the flange 314 will cause the displacement member 174 attached thereto to rotate and be radially displaced. Sufficient radial displacement of the displacement member 174 will cause the valve stem 118 to rotate, the valve assembly within the container 26 to open, and for fluid to be dispensed from the overcap 300. In the present embodiment, a half turn of the third gear 166 and the cam extension 310 is sufficient to open the valve assembly of the container 26. However, in other embodiments the drive unit 152 and the displacement member 174 may be modified to effect a dispensing of fluid based on a greater or lesser rotation of any of the above noted elements.

Figure 19:
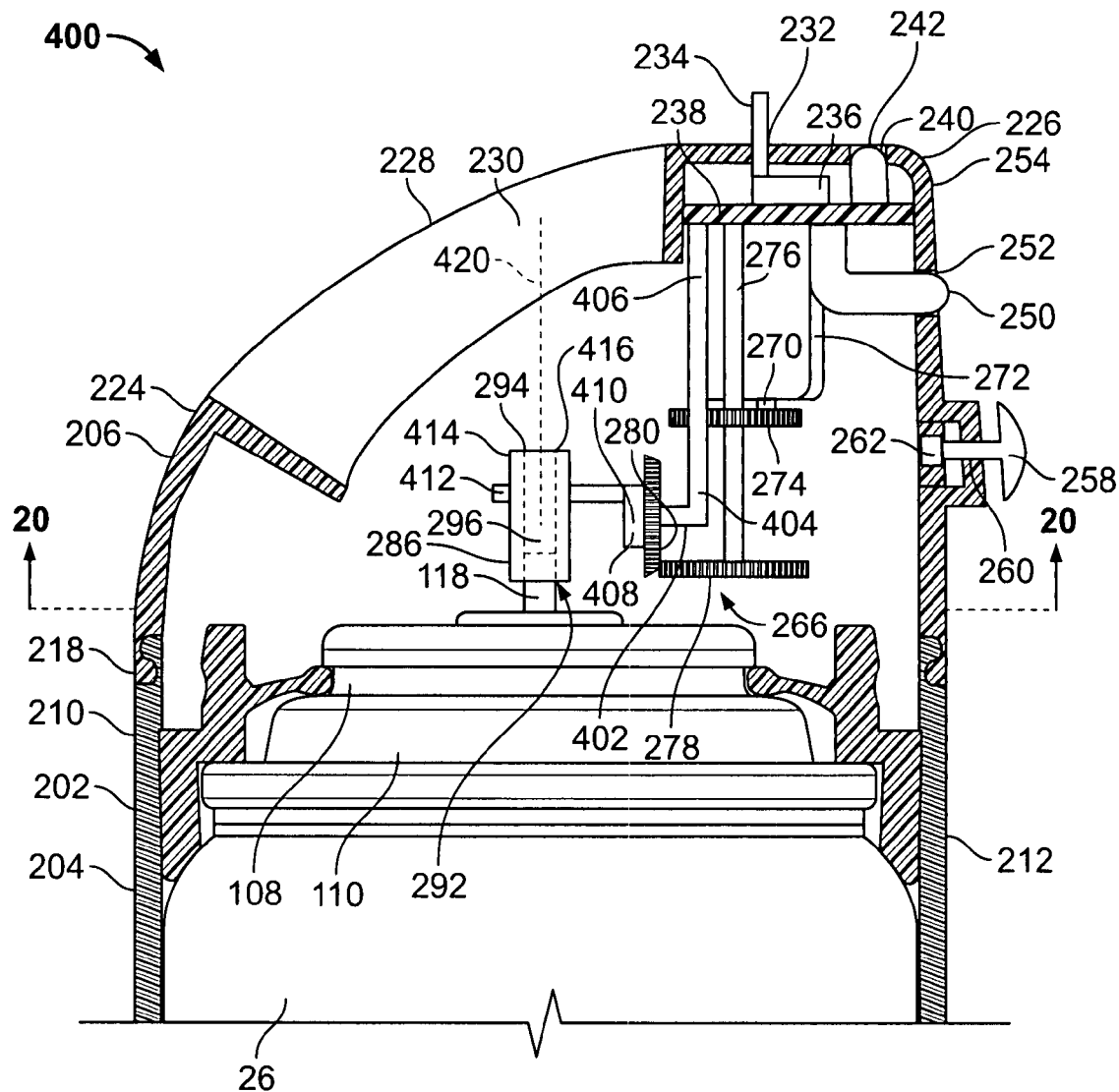
FIG. 19 is a partial sectional view of still another embodiment of a dispensing system taken generally along the lines 19-19 of FIG. 14, which is similar to the system depicted in FIG. 15 except for a change to a drive unit and a displacement member.
Figure 20:
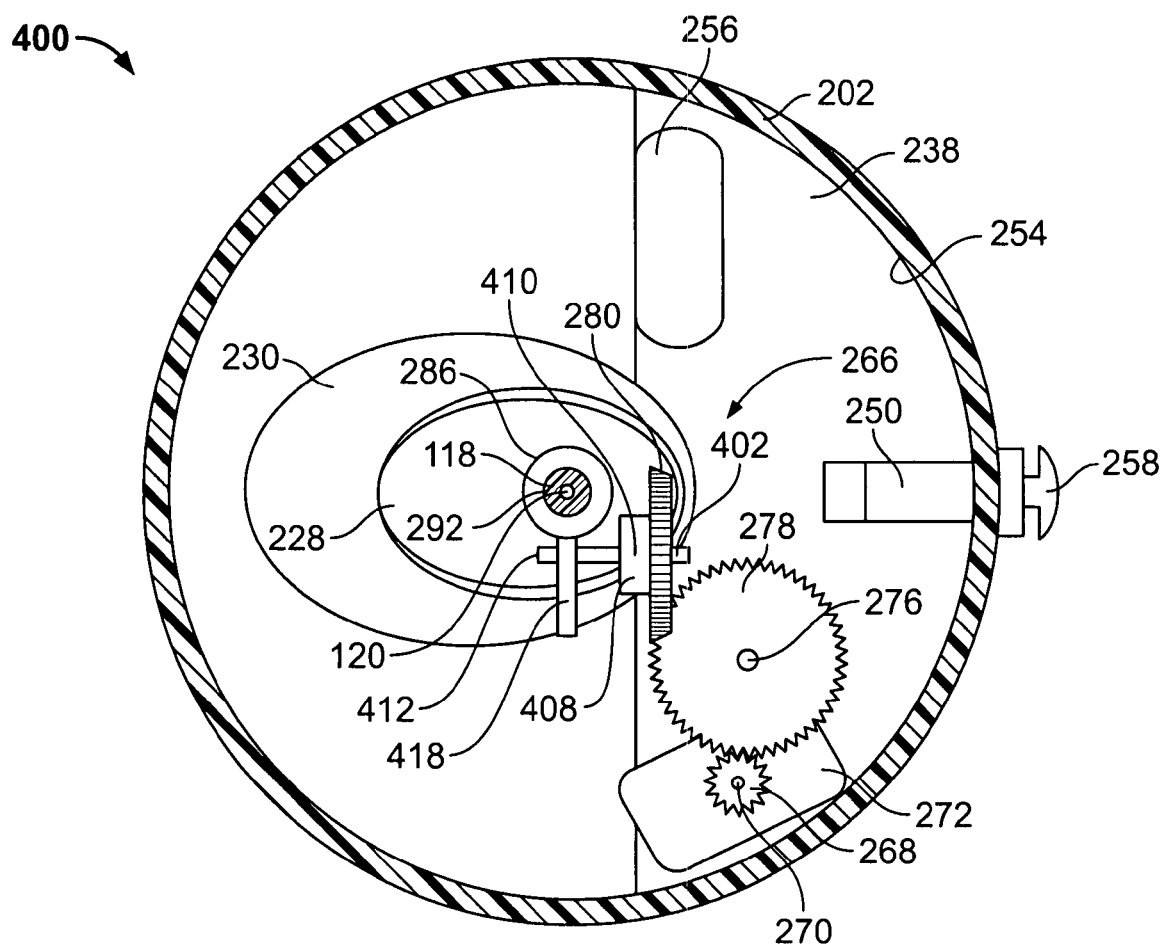
FIG. 20 is a sectional view taken generally along the lines 20-20 of FIG. 19.

FIGS. 19 and 20 depict yet another embodiment of a dispensing system 400 similar to the one shown in FIGS. 14-16. However, in the present embodiment, the second transfer gear 278 is spaced from the first transfer gear 274 on the first transfer shaft 276. Further, the third transfer gear 280 is fixedly mounted to a shaft 402 that extends generally transversely from a distal end 404 of a connector 406. The connector 406 is attached to the platform 238. The electric motor 272, the main drive gear 268, and the first through third transfer gears 274, 278, 280 are all in mechanical communication to cause the rotation of an actuating cam 408, which is provided in a similar manner as the actuating cam of FIGS. 17 and 18. The actuating cam 408 includes a base member 410 fixedly mounted to the shaft 402. A cam extension 412 is disposed on the base member 410 in a manner that is off-centered from the shaft 402 and a center of the third transfer gear 280.

The displacement member 286 depicted in FIGS. 15 and 16 has also been modified for purposes of the present embodiment. The present embodiment of the displacement member 286 comprises a substantially uniformly cylindrical portion 414, wherein the aperture 294 is disposed on an upper end 416 of the displacement member 286 in fluid communication with the opening 292 by the conduit 296. A rectangular flange 418 extends substantially transversely from the cylindrical portion 414 with respect to a longitudinal axis 420 of the displacement member 286. In a non-actuation position, the cam extension 412 is positioned out of contact with the flange 418 or in contact to a degree insufficient to radially tilt the dispensing member 286 to actuate the valve stem 118. When the drive unit 266 is activated, power is transferred through the first through third transfer gears 274, 278, 280. Rotation of the third gear 280 causes the cam extension 412 to similarly rotate and impinge against a length of the flange 418. Impingement of the flange 418 will cause the displacement member 286 attached thereto to rotate and be radially displaced. Sufficient radial displacement of the displacement member 286 will cause the valve stem 118 to rotate, the valve assembly within the container 26 to open, and for fluid to be dispensed from the overcap 400.

It is anticipated that any of the drive units 152, 266 described herein will be driven for an appropriate duration to provide radial displacement to the valve stem 118. The valve stem 118 actuates with each corresponding radial displacement. Preferably, although not necessarily, the valve stem 118 is radially displaced to a discharge position for a predetermined length of time ("spraying period"). The duration of the spraying period is typically equal to about 170 milliseconds. Indeed, if desired, the valve stem 118 could be radially displaced to the discharge position until all of the container contents are exhausted. Further, the valve stem 118 may be radially displaced during each of multiple spraying periods in response to the occurrence of a single activation signal, wherein the spraying periods are separated by rest periods. Multiple spraying periods may be beneficial when a single extended spraying period from a container is undesirable or when intermittent discharge is desired.

Figure 21:
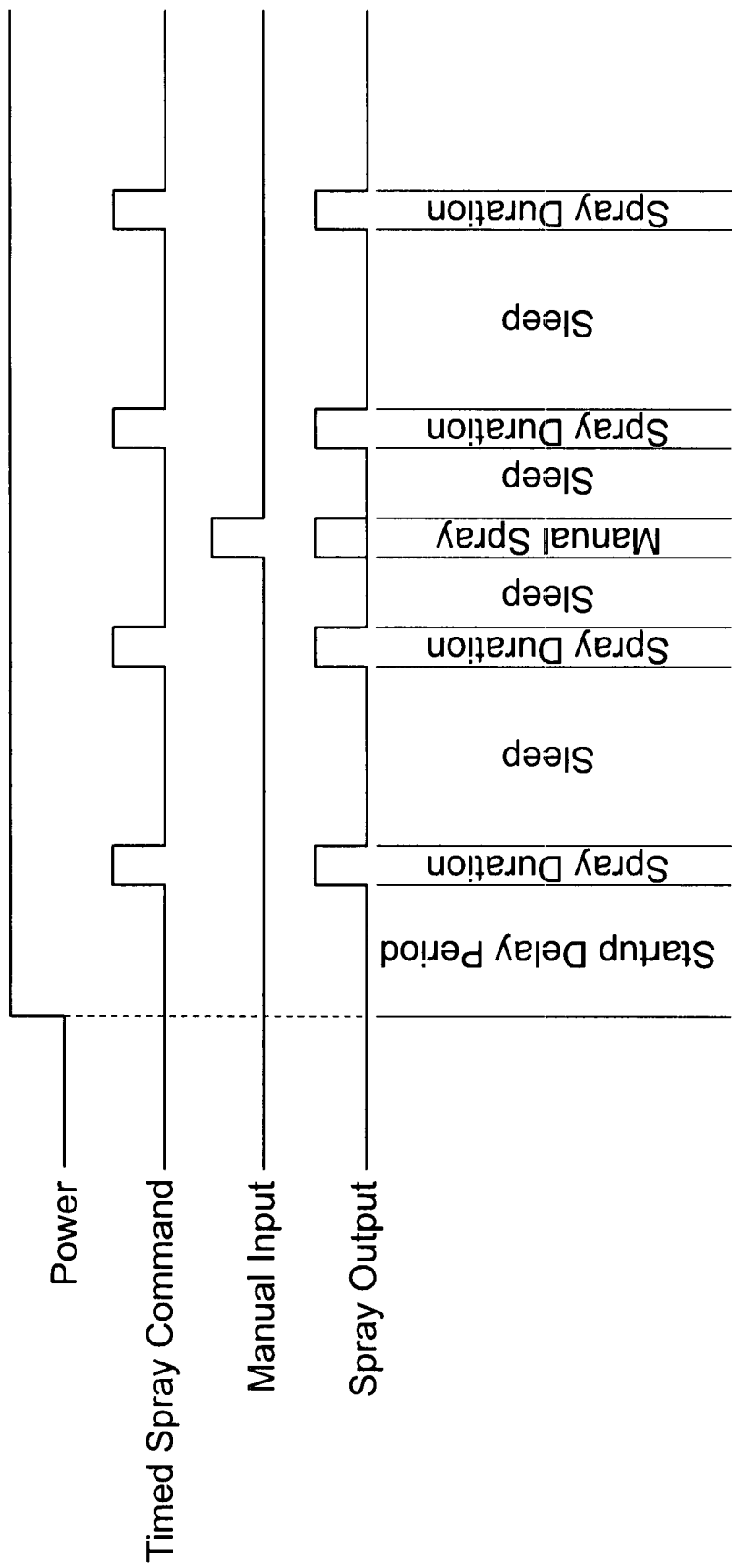
FIG. 21 is a timing diagram illustrating the operation of the overcap of FIGS. 1-12 according to a first operational sequence.

FIG. 21 depicts a timing diagram illustrative of an operational sequence of the overcap 10 during an in use condition. Initially, the overcap 10 is energized by moving the finger 196 from an "OFF" position to one of four operating modes 500, 502, 504, 506, whereupon the overcap 10 enters a startup delay period. Each of the four operating modes 500, 502, 504, 506 corresponds to a predetermined sleep period between consecutive spraying periods. For example, the first operating mode 500 may correspond to a five minute sleep period, the second operating mode 502 may correspond to a seven and a half minute sleep period, the third operating mode 504 may correspond to a fifteen minute sleep period, and the fourth operating mode 506 may correspond to a thirty minute sleep period. For the present example, we shall assume the first operating mode 500 has been chosen. Upon completion of the startup delay period, the drive unit 152 is energized to discharge fluid from the overcap 10 during a first spraying period. The startup delay period is preferably about three seconds long, and the spraying period is typically about 170 milliseconds long. Upon completion of the first spraying period, the overcap 10 enters a first sleep period that lasts 5 minutes. Upon expiration of the first sleep period the drive unit 152 is energized to discharge fluid during a second spraying period. Thereafter, the overcap 10 enters a second sleep period that lasts for 5 minutes. In the present example, the second sleep period is interrupted by the manual activation of the overcap 10, whereupon fluid is dispensed during a third spraying period. Automatic operation thereafter continues with alternating sleep and spraying periods. At any time during a sleep period, the user may manually actuate the overcap 10 for a selectable or fixed period of time by depressing the pushbutton 34. Upon termination of the manual spraying operation, the overcap 10 completes the pending sleep period. Thereafter, a spraying operation is undertaken.

Figure 22:
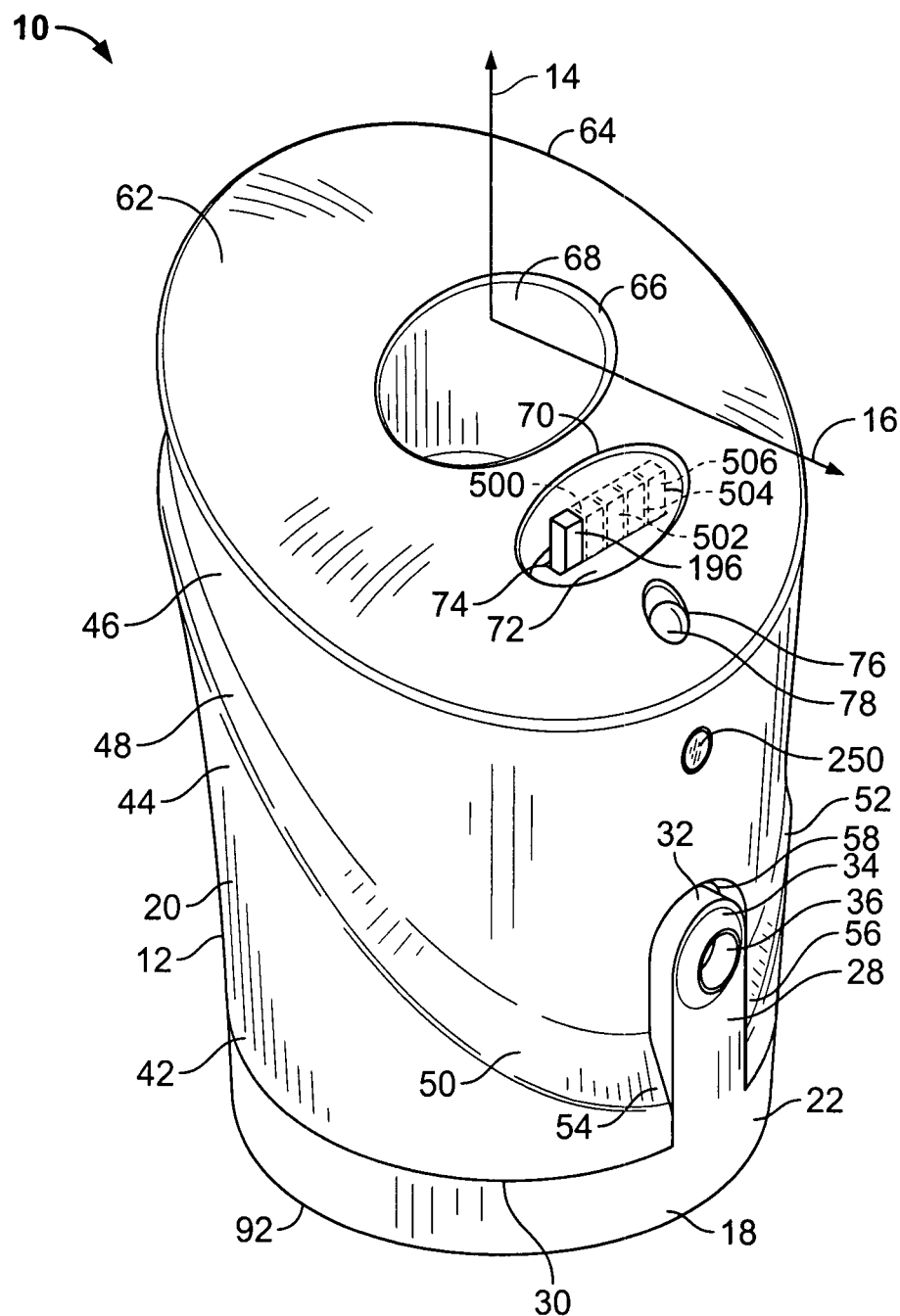
FIG. 22 is another embodiment of an overcap, which is similar to the one shown in FIG. 1 except for the addition of a sensor.

In another embodiment not shown, the switch assembly 194 may have a continuous range of settings instead of the four distinct operating modes 500, 502, 504, 506 described above. In such an embodiment, the switch assembly 194 may be provided with a switch mechanism, for example a dial (not shown), that provides for continuous user variation of the spraying period and/or the sleep period between a continuous spray and periods lasting several hours or days. In a further embodiment, the switch assembly 194 may be replaced and/or supplemented by the sensor 250, e.g., a photocell motion sensor. The photocell collects ambient light and allows the control circuit to detect any changes in the intensity thereof. Filtering of the photocell output is undertaken by the control circuit. If the control circuit determines that a threshold light condition has been reached, e.g., a predetermined level of change in light intensity, the control circuit develops a signal to energize the drive unit 152. For example, if the overcap 10 is provided with the sensor 250 (see FIG. 22) and placed in a lit bathroom, a person walking past the sensor may block a sufficient amount of ambient light from reaching the sensor to cause the control circuit to energize the drive unit 152 and discharge a fluid. Other motion detectors known to those of skill in the art may also be utilized e.g., a passive infrared or pyro-electric motion sensor, an infrared reflective motion sensor, an ultrasonic motion sensor, or a radar or microwave radio motion sensor.

The LED 198 illuminates the light transmissive rod 78 when the overcap 10 is in an operative state. The LED 198 blinks intermittently once every fifteen seconds during the sleep period. Depending on the selected operating mode, the blinking frequency of the LED 198 begins to increase as a spraying period becomes imminent. The more frequent illumination of the LED 198 serves as a visual indication that the overcap 10 is about to discharge fluid contents into the atmosphere.

It is also envisioned that the switch assembly 194 may be replaced or supplemented with a vibration sensor, an odor sensor, a heat sensor, or any other environmental sensor known to those skilled in the art. Alternatively, more than one environmental sensor may be provided in the overcap in lieu of the switch assembly 194 or in combination with same. It is anticipated that one skilled in the art may provide any type of environmental sensor either alone or in combination with the switch assembly 194 and/or other sensors to meet the needs of a user. In one particular embodiment, the switch assembly 194 and the environmental sensor 250 are provided in the same overcap. In such an embodiment, a user may choose to use the timer-based switch assembly 194 to automatically operate the drive unit 152 of the overcap, or the user may choose to use the environmental sensor 250 to detect a given event prior to activating the overcap. Alternatively, the overcap may operate in a timer and sensor based mode of operation concurrently.

Any of the embodiments described herein may be modified to include any of the structures or methodologies disclosed in connection with different embodiments. Further, the present disclosure is not limited to aerosol containers of the type specifically shown. Still further, the overcaps of any of the embodiments disclosed herein may be modified to work with any type of aerosol or non-aerosol container having a tilt-activated valve stem.

INDUSTRIAL APPLICABILITY

Aerosol dispensers are commonly used to dispense volatile materials such as air fresheners, deodorants, insecticides, germicides, decongestants, perfumes, and the like, that are stored within aerosol containers. Automated valve activation systems for aerosol containers allow the contents thereof to be released without human interaction, for example, according to a predetermined time schedule. Tilt-activated valve stems for aerosol container release valves typically require less force to operate than vertically activated valve stems. A system for activation of a tilt-activated valve stem that includes a drive unit that is controlled by a timing circuit and/or a sensor is presented. The system may be installed in a typical overcap for use with ordinary tilt-activated containers, resulting in an improvement in utility of the aerosol dispenser.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:
1. A volatile material dispensing system, comprising:
a housing releasably mounted on a container having a tilt-activated valve stem;
a displacement member disposed within the housing, wherein a first end of the displacement member is disposed on the tilt-activated valve stem and a second end is in fluid communication with the first end and includes a discharge conduit that extends axially from the first end along a longitudinal axis of the displacement member, and wherein a flange extends radially from the displacement member; and
a drive unit disposed within the housing, wherein the drive unit includes a camming member that impinges the flange of the displacement member and radially displaces the displacement member in response to an electronic activation signal, and wherein the camming member is mounted on a transfer shaft that is substantially transverse to the longitudinal axis and offset from a plane that runs through the longitudinal axis and the flange.

2. The dispensing system of claim 1, wherein the radial displacement of the displacement member causes the radial displacement of the tilt-activated valve stem.

3. The dispensing system of claim 1 further including a discharge orifice within an upper surface of the housing, wherein the discharge orifice is in fluid communication with the second end of the displacement member.

4. The dispensing system of claim 1, wherein the displacement member is substantially cylindrical.

5. The dispensing system of claim 3, wherein the radial displacement of the displacement member causes fluid to be discharged from the container in a direction substantially parallel to the longitudinal axis of the displacement member.

\* \* \* \* \*